(12) United States Patent
Murata

(10) Patent No.: US 7,862,772 B2
(45) Date of Patent: Jan. 4, 2011

(54) ANALYZER-SUPPLYING DEVICE

(75) Inventor: Yasuhito Murata, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 978 days.

(21) Appl. No.: 10/576,429

(22) PCT Filed: Oct. 19, 2004

(86) PCT No.: PCT/JP2004/015414

§ 371 (c)(1), (2), (4) Date: Apr. 20, 2006

(87) PCT Pub. No.: WO2005/040834

PCT Pub. Date: May 6, 2005

(65) Prior Publication Data

US 2007/0071644 A1 Mar. 29, 2007

(30) Foreign Application Priority Data

Oct. 22, 2003 (JP) .............................. 2003-362420

(51) Int. Cl.
*G01N 33/48* (2006.01)
(52) U.S. Cl. ........................... 422/63; 422/61; 422/104; 436/44; 436/165; 436/808; 221/191; 221/232; 221/233; 221/234
(58) Field of Classification Search .................. 422/61, 422/63, 104; 436/44, 165, 808; 221/191, 221/232–234
See application file for complete search history.

(56) References Cited

U.S. PATENT DOCUMENTS

| 4,876,204 | A | 10/1989 | Inoue et al. |
| 5,470,533 | A | 11/1995 | Shindo et al. |
| 5,556,597 | A | 9/1996 | Shindo et al. |
| 2002/0057993 | A1* | 5/2002 | Maisey et al. ............ 422/82.01 |

FOREIGN PATENT DOCUMENTS

| JP | 62-104606 | 5/1987 |
| JP | 5-264540 | 10/1993 |
| JP | 11-118808 | 4/1999 |
| JP | 2000-35433 | 2/2000 |
| JP | 6-324057 | 5/2000 |

* cited by examiner

*Primary Examiner*—Lyle A Alexander
(74) *Attorney, Agent, or Firm*—Hamre, Schumann, Mueller & Larson, P.C.

(57) ABSTRACT

The present invention relates to a test piece supplying device (1) comprising a container (4) for containing a plurality of test pieces, and also includes a movable body (3) moving relative to the container (4) with the test piece accommodated in a recess (30) so as to take the test piece out of the container (4). The container (4) includes a sweeping portion (41) for interfering with the test pieces, in the container (4), located above the test piece accommodated in the recess (30), when the movable body (3) moves relative to the container (4). When a warped test piece accommodated in the recess (30) is moved relative to the container (4), the interfering portion (41) flattens the test strip to be accommodated in the recess (30) so that the test piece is easily taken out of the container (4).

17 Claims, 21 Drawing Sheets

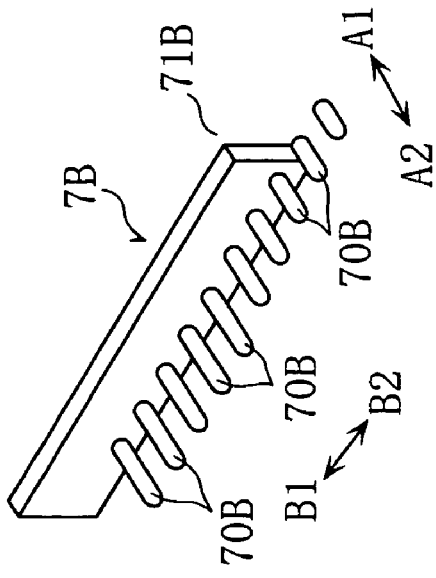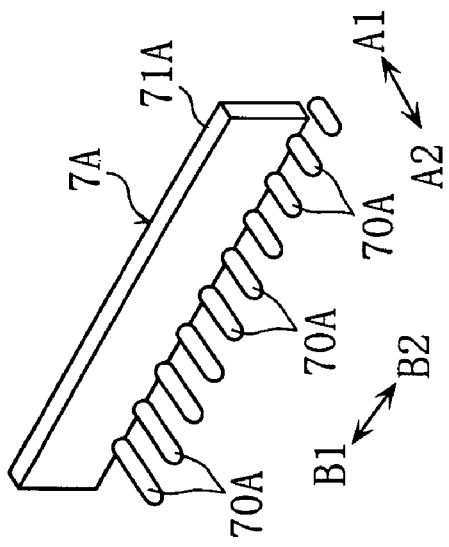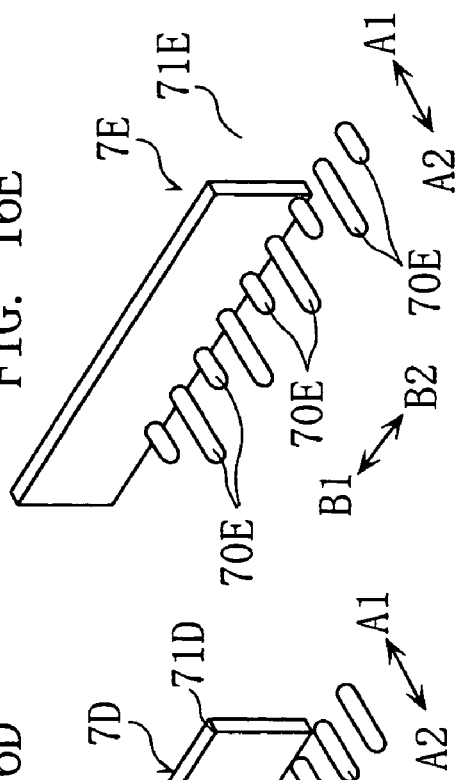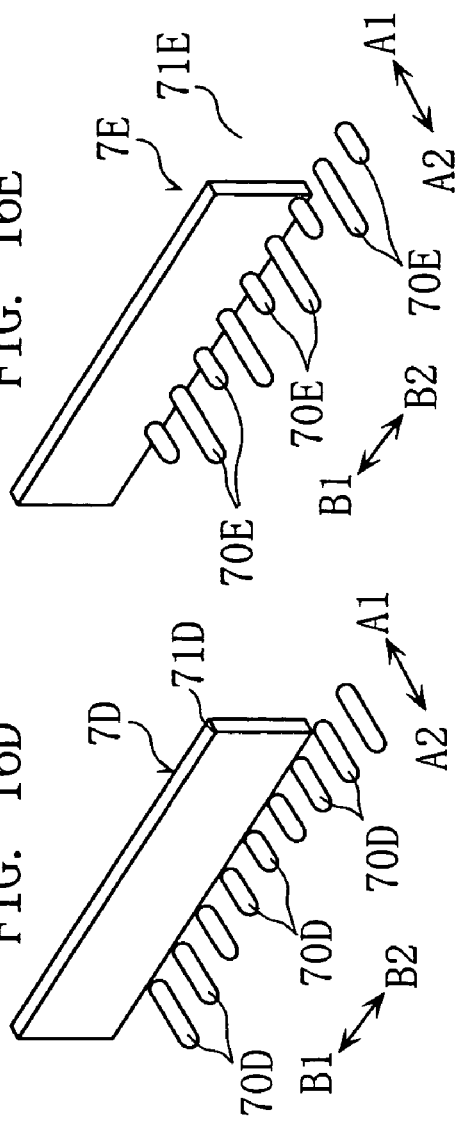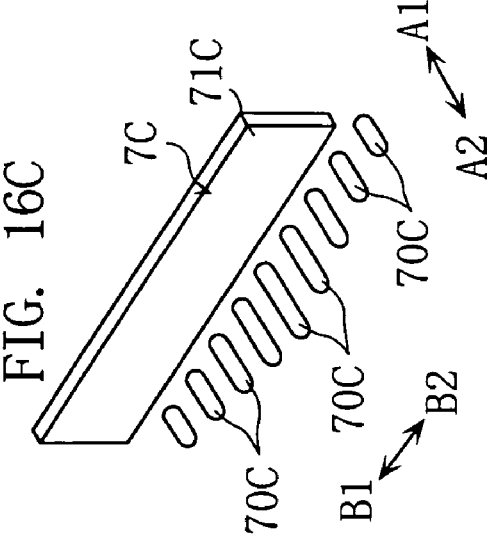

ANALYZER-SUPPLYING DEVICE

TECHNICAL FIELD

The present invention relates to a test piece supplying device provided with a container that accommodates a plurality of test pieces, where the device is configured to pick an individual test piece from the container and transfer it to the desired site.

BACKGROUND ART

Urine analysis is performed by utilizing an optical method, for example, whereby the reagent pad of a test piece is impregnated with urine, and then the color change of the pad is observed. Specifically, to check the coloring at the reagent pad, the test piece is first transferred to a portion where urine is dropped onto the reagent pad, and then transferred to an optical checking position. The test piece can be transferred to the urine application portion by utilizing a test piece supplying device (refer to Patent documents 1 and 2 listed below).

An example of such test piece supplying device is illustrated in FIGS. 21 and 22A. The illustrated test piece supplying device 9 includes a container 91 containing a plurality of test pieces 90A, 90B, and also includes a movable body 92 for taking one test piece 90A at a time out of the container. The container 91 is provided with a blade 93 for preventing more than one test piece 90A, 90B from being simultaneously taken out of the container 91. The movable body 92 is formed with a groove 92a for accommodating one test piece 90A.

As shown in FIG. 22A, in the test piece supplying device 9, the movable body 92 is moved to position the groove 92a at a site corresponding to the container 91, so that the test piece 90A is accommodated in the groove 92a. Then, as shown in FIGS. 22B and 22C, the movable body 92 is moved in the direction A, and the test piece 90A is taken out of the container 91. Here, in the container 91, the blade 93 sweeps away the test pieces 90B above the test piece 90A accommodated in the groove 92a, so that only the test piece 90A in the groove 92a is taken out of the container 91. In this way, the test piece 90A is taken out of the container and then is moved by the movable body 92 further in the direction A, to be supplied to a destination such as an optical checking position.

Generally, the test pieces 90A, 90B are stored together in a bottle. If the storing condition is not good, some of the test pieces 90A, 90B may undergo plastic deformation and may be warped (see 90A' in FIG. 23). As shown in FIG. 23, when placing such warped test piece 90A' into the groove 92a of the movable body 92, the test piece 90A' is not fully accommodated within the groove 92a, and a part of the test piece 90A' may protrude from the groove 92a. In this state, when the movable body 92 moves in the direction A, the blade 93 interferes with the portion of the test piece 90A' protruding out of the groove 92a, and scrapes the test piece 90A' off the groove 92a. In other words, the warped test piece 90A' cannot be taken out of the container 9 of the test piece supplying device 9. As seen from this, in the test piece supplying device 9, when a warped test piece 90A' is contained in the container 9, the probability of taking out the test pieces 90A, 90A', 90B (the rate of the number of success to the total number of the taking-out trials) is reduced, and thus the number of the test pieces 90A, 90A', 90B to be taken out per unit time is reduced.

Patent Document: JP-A-11-118808

Patent Document: JP-A-2000-35433

DISCLOSURE OF THE INVENTION

An object of the present invention is to provide a test piece supplying device for taking test pieces out of a container containing a plurality of test pieces one by one, and for transferring it to a destination, so that the number of test pieces taken out of the container per unit time is increased, and that the probability of taking the test pieces out of the container is reduced as less as possible, even if a warped test piece is contained in the container.

A test piece supplying device according to the present invention comprises a container for containing a plurality of test pieces and a movable body formed with a recess for accommodating one of the test pieces contained in the container. When the test piece is accommodated in the recess, the movable body moves relative to the container so that the test piece is taken out of the container one by one, the container includes sweeping means for interfering with the test pieces located above the test piece accommodated in the recess, so that only one test piece is selectively accommodated in the recess when the movable body moves relative to the container. When the movable body moves relative to the container with a warped test piece accommodated in the recess, the sweeping means flattens the test strip to be accommodated in the recess so that the test piece is easily taken out of the container.

For example, the interfering or sweeping means includes a plate extending in a direction (e.g. a horizontal direction) intersecting with the vertical direction, and interfering with the test pieces above the test piece accommodated in the recess.

For example, the recess is elongated in a direction perpendicular to the transfer direction of the test piece. In this case, the plate includes an interference surface for interfering with the test pieces above the test piece accommodated in the recess, and the interference surface has a portion non-parallel to the elongated recess. Preferably, the interference surface includes a linear portion inclined to the elongated recess, or a curved portion.

The interfering means may include a plurality of interference portions projecting in a direction (e.g. a horizontal direction) intersecting with the vertical direction, and interfering with the test pieces above the test piece accommodated in the recess.

At least a part of the plurality of interference portions project by different distances. For example, the recess is elongated in a direction perpendicular to the transfer direction of the test piece, and at least apart of the plurality of interference portions are arranged so that shortest distances between tip ends of the interference portions and the recess are different from each other. Preferably, the part of the plurality of interference portions are arranged in a straight or substantially straight line inclined relative to the elongated recess, or in a curve or a substantially curved line.

For example, the interfering means includes a plate extending in a direction perpendicular to the transfer direction, and the plurality of interference portions are provided by forming a plurality of cutouts at the plate.

The plurality of interference portions may also be provided by fixing a plurality of pins to the interfering means.

The interfering means may be provided with a plurality of pins projecting downward. In this case, when the recess is elongated in the direction perpendicular to the transfer direction of the test piece, at least a part of the plurality of pins are arranged, so that the shortest distances between tip ends of the pins and the recess are different from each other, in a straight line or a substantially straight line inclined relative to the elongated recess, or in a curve or a substantially curved line.

The movable body moves horizontally or rotates to take the test piece out of the container.

BRIEF DESCRIPTION OF THE DRAWINGS

FIG. 3B is a sectional view of a principal part of the test piece supplying device of FIG. 1 for illustrating its function.

FIG. 4B is a sectional view of a principal part of the test piece supplying device of FIG. 1 for illustrating its function.

FIG. 5B is a sectional view of a principal part of the test piece supplying device of FIG. 1 for illustrating its function.

FIG. 16A-E is a perspective view illustrating another example of the sweeping means.

BEST MODE FOR CARRYING OUT THE INVENTION

Figure 1:
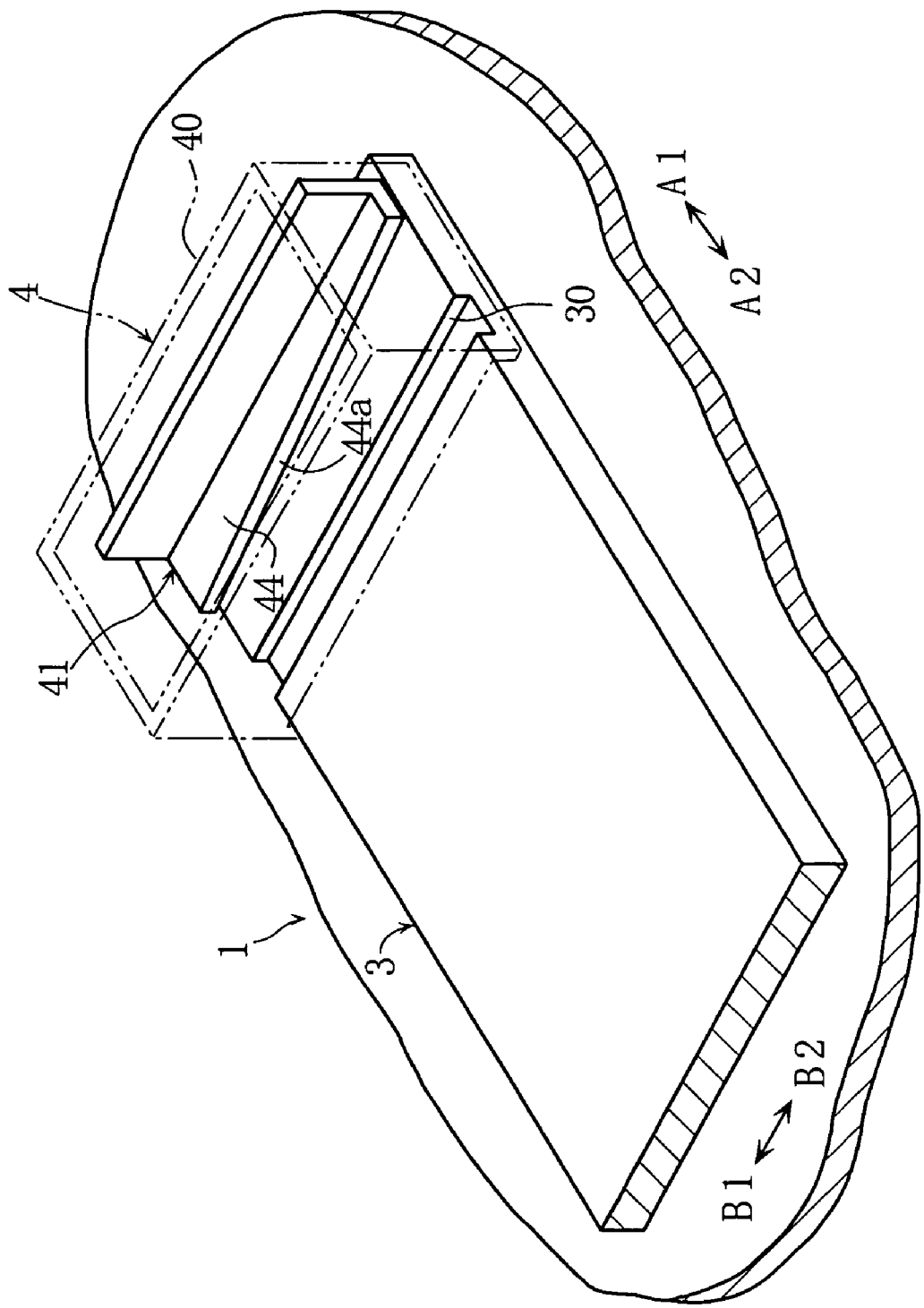
FIG. 1 is an overall perspective view illustrating, partly transparently, an example of a test piece supplying device according to the present invention.

FIG. 1 illustrates a test piece supplying device 1 which may be incorporated in or attached to an analyzing device in use, and the device transfers test pieces 2A, 2A', 2B in the A1 direction, as shown in FIGS. 2A-2C and 3A, to supply these test pieces to e.g. an optical checking position. The test piece supplying device 1, including a movable body 3 and a container 4, is configured to supply the test pieces 2A, 2A', 2B each including a strip-shaped base 20 provided with a plurality of reagent pads 21.

Figure 2A:
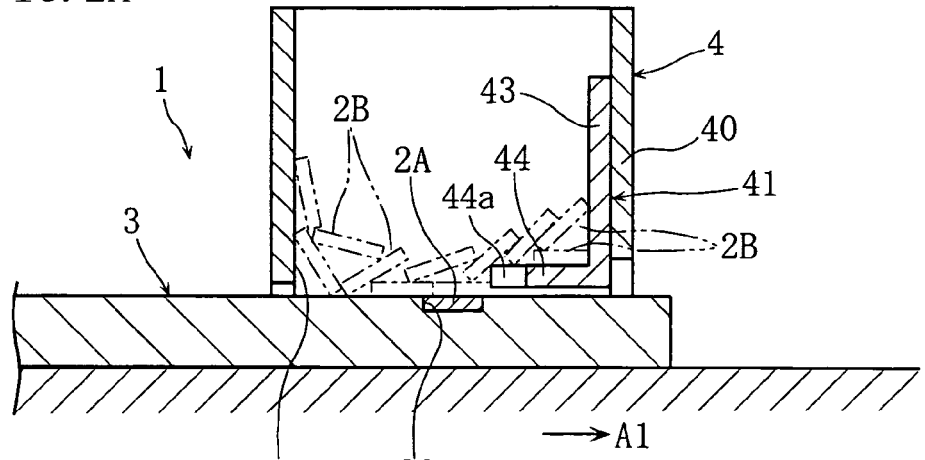
FIG. 2A-C is a sectional view of a principal part of the test piece supplying device for illustrating its function.
Figure 2B:
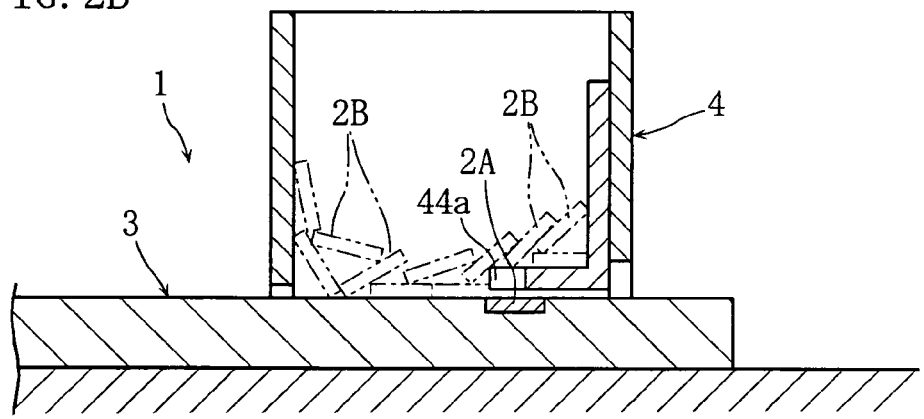
Figure 2C:
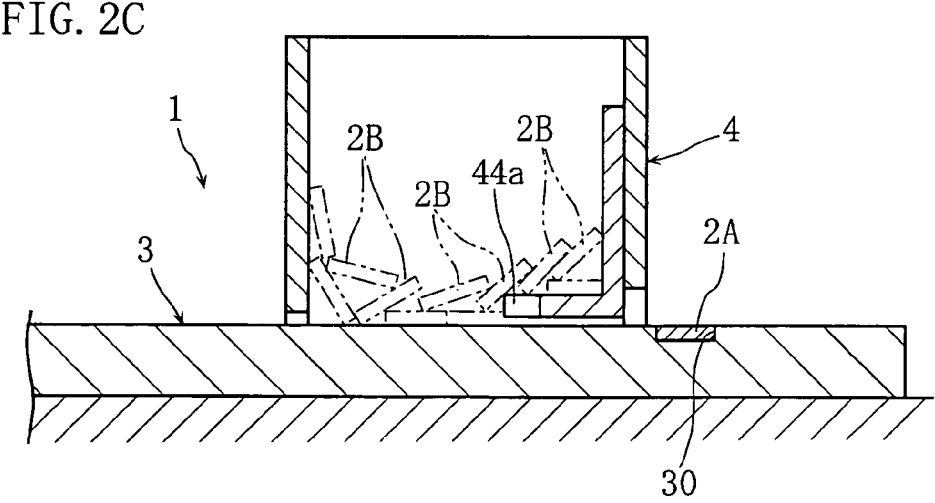

As shown in FIG. 1, the movable body 3 includes a recess 30 for accommodating the test pieces 2A, 2B, and is movable relative to the container 4 in the directions A1, A2. The recess 30 is formed into dimensions corresponding to the outer configuration of the test pieces 2A, 2B, and is elongated in the directions B1, B2 perpendicular to the directions A1, A2. By moving the movable body 3 in the directions A1, A2, the recess 30 is moved between two positions, one of which is within the container 4 as shown in FIG. 2A, and the other is exposed out of the container 4 as shown in FIG. 2C. The movable body 3 is moved by a drive source such as a non-illustrated motor.

As shown in FIGS. 1 and 2A, the container 4 contains a plurality of test pieces 2A, 2B, and includes a body 40 serving as side surfaces of the container 4. The container 4 further includes sweeping means 41 and a bottom opening 42.

In taking the test pieces 2A, 2B out of the container 4, the sweeping means 41 works so that more than one of the test pieces 2A, 2B are not taken out simultaneously. The sweeping means 41 includes an attaching portion 43 attached to the body 40 and a sweep function portion 44 extending in the direction A2. The sweep function portion 44 is a plate whose dimension measured in the direction A1 or A2 is reduced as proceeding in the direction B2. In other words, the sweep function portion 44 includes an interference surface 44a that is non-parallel to the elongated recess 30 of the movable body 3. When moving the movable body 3 in the direction A1 to position the recess 30 out of the container 4, the interference surface 44a interferes with the test piece 2B above the test piece 2A accommodated in the recess 30, and removes the test piece 2B therefrom. In this way, the test piece supplying device 1 can take the test piece 2A out of the container 4 by accommodating the test piece 2A in the recess 30 so that only this test piece 2A is allowed to pass below the sweep function portion 44.

The test pieces 2A, 2B contained in the container 4 contact the movable body 3 through the bottom opening 42 that is closed by the movable body 3. The interference surface 44a substantially defines an end of the bottom opening 42 at the side of the direction A1.

Next, the operation of taking out and transferring the test piece in the test piece supplying device 1 is described with reference to FIGS. 2A-2C.

As shown in FIG. 2A, in the test piece supplying device 1, the recess 30 of the movable body 3 is brought to a position within the container 4, and the test piece 2A is accommodated in the recess 30. When the movable body 3 is moved in the direction A1 from the above-mentioned position, the interference surface 44a of the sweep function portion 44 interferes with and sweeps away the test pieces 2B above the test piece 2A accommodated in the recess 30. At this stage, the test piece 2A accommodated in the recess 30 does not come into contact with the interference surface 44a, but passes below the sweep function portion 44 as the movable body A1 moves in the direction A1, and is taken out of the container 4. By further moving the movable body 3 in the direction A1, the test piece 2A taken out of the container is next supplied to the desired site such as an optical checking position.

Figure 3A:
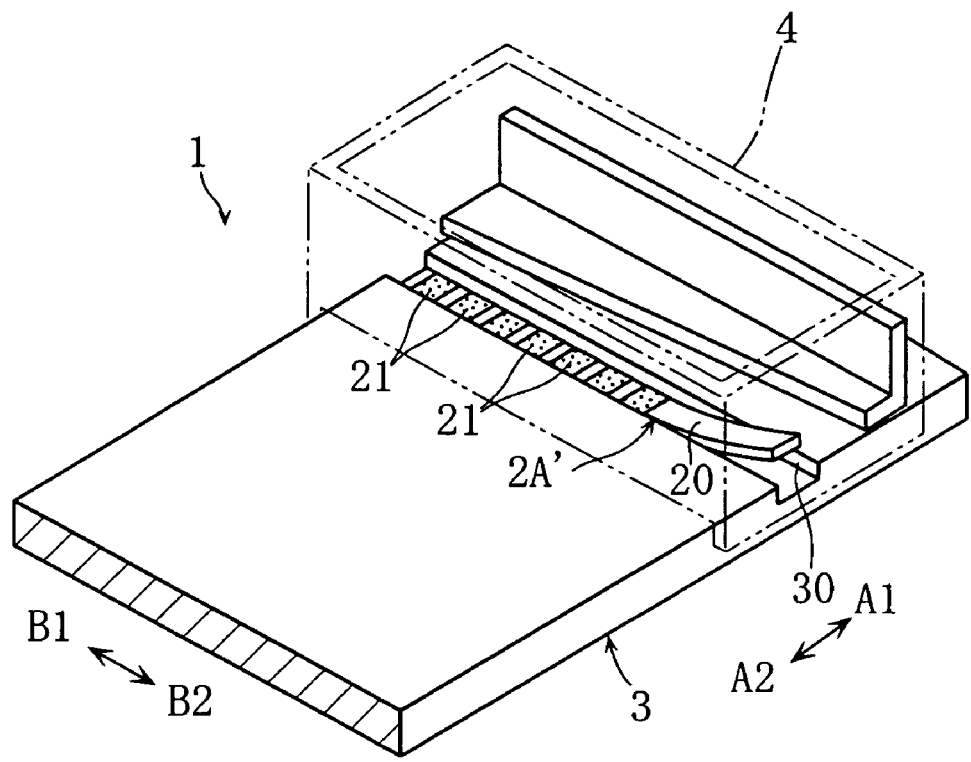
FIG. 3A-B is a perspective view of a principal part of the test piece supplying device of FIG. 1 for illustrating its function.
Figure 3B:
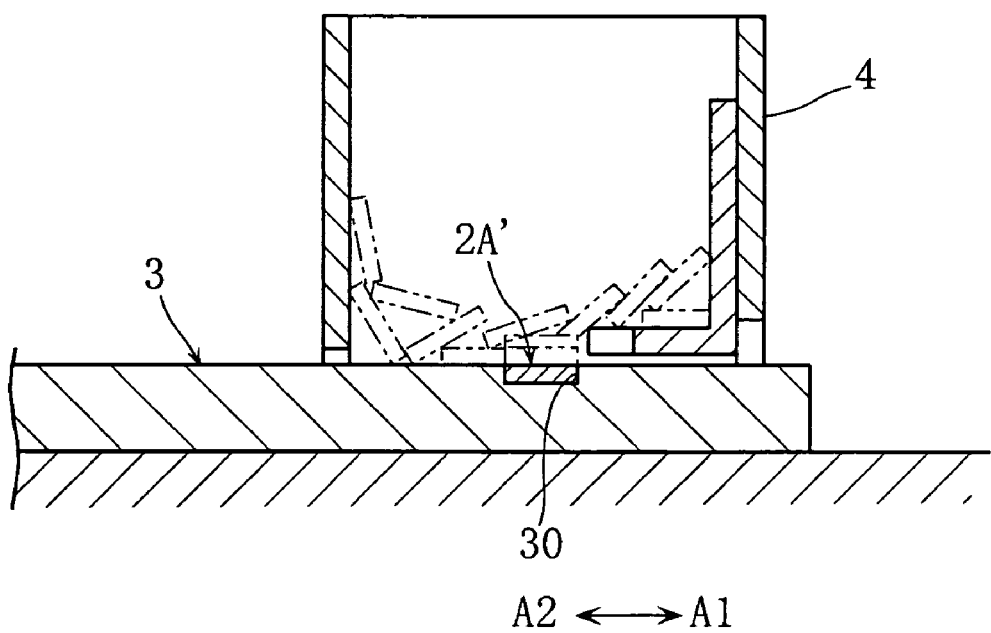
Figure 4A:
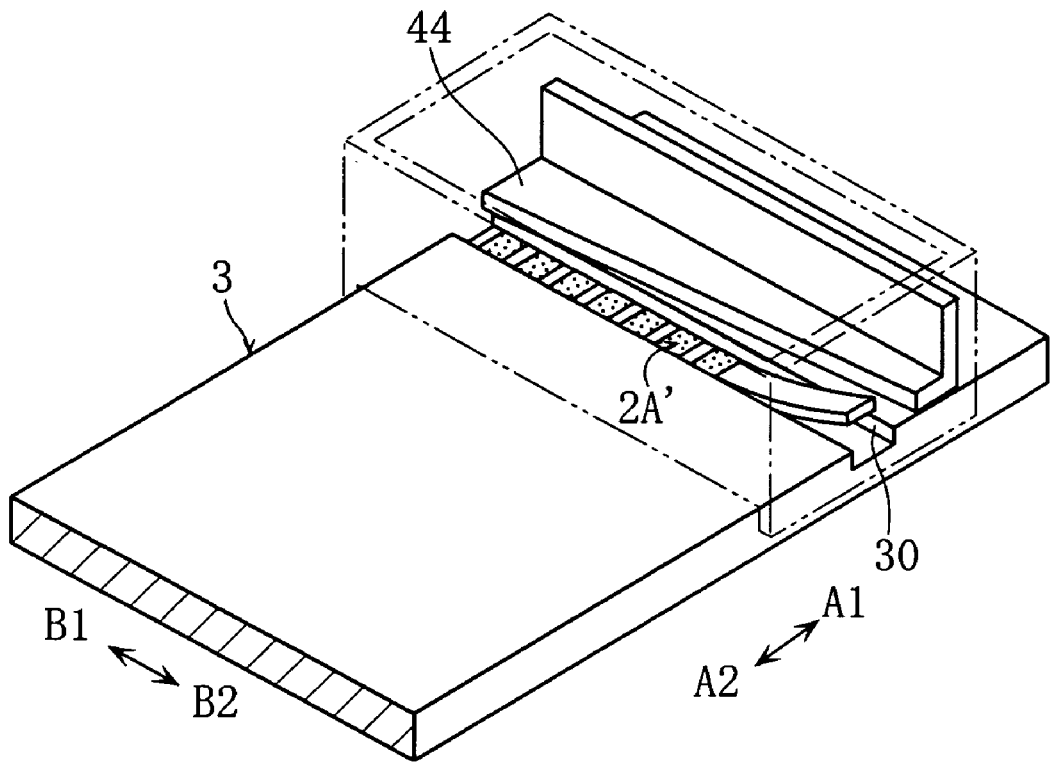
FIG. 4A-B is a perspective view of a principal part of the test piece supplying device of FIG. 1 for illustrating its function.
Figure 4B:
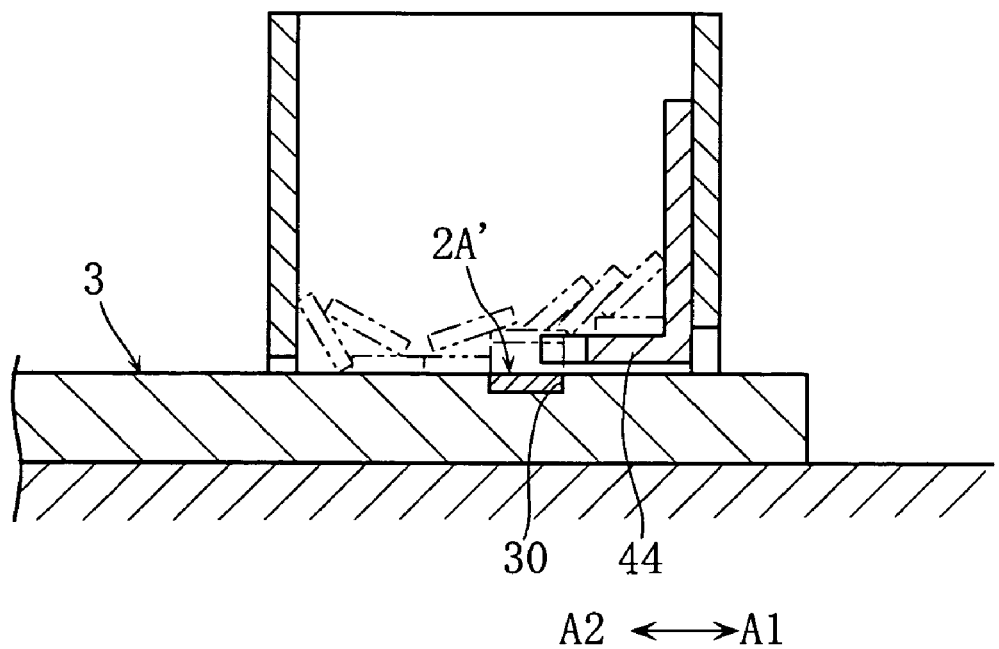
Figure 5A:
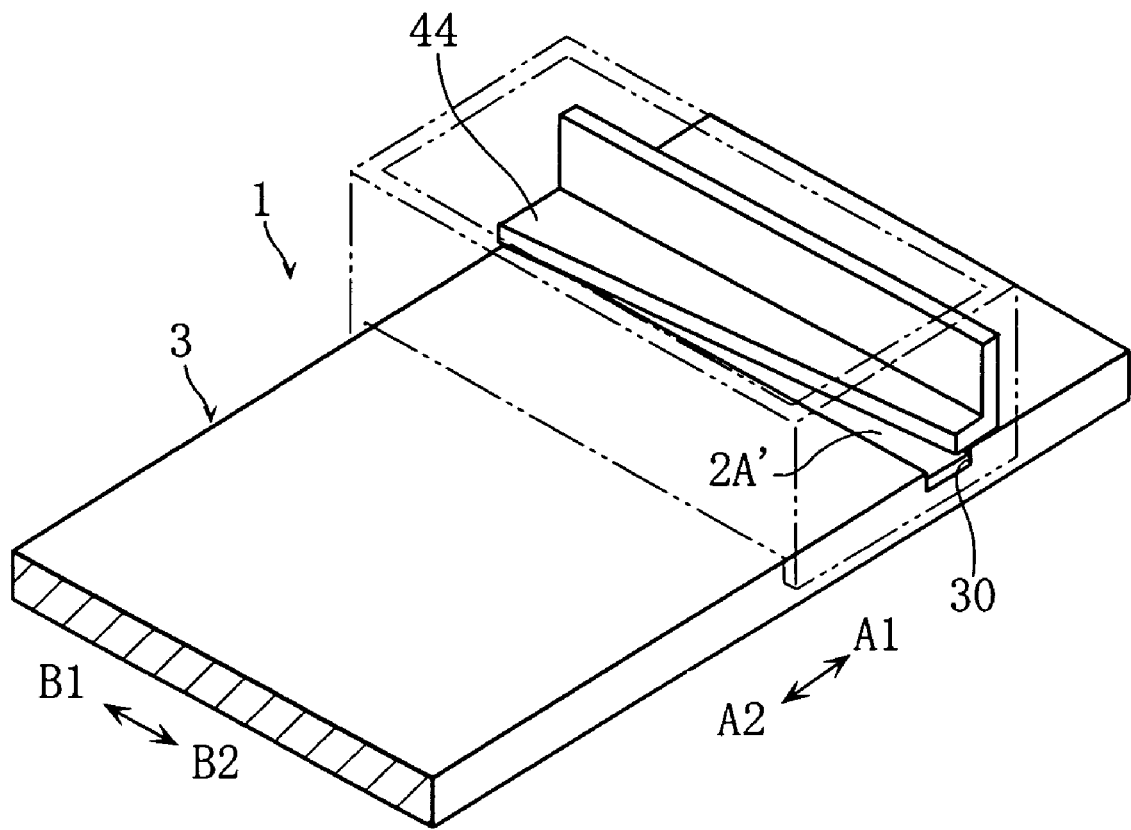
FIG. 5A-B is a perspective view of a principal part of the test piece supplying device of FIG. 1 for illustrating its function.
Figure 5B:
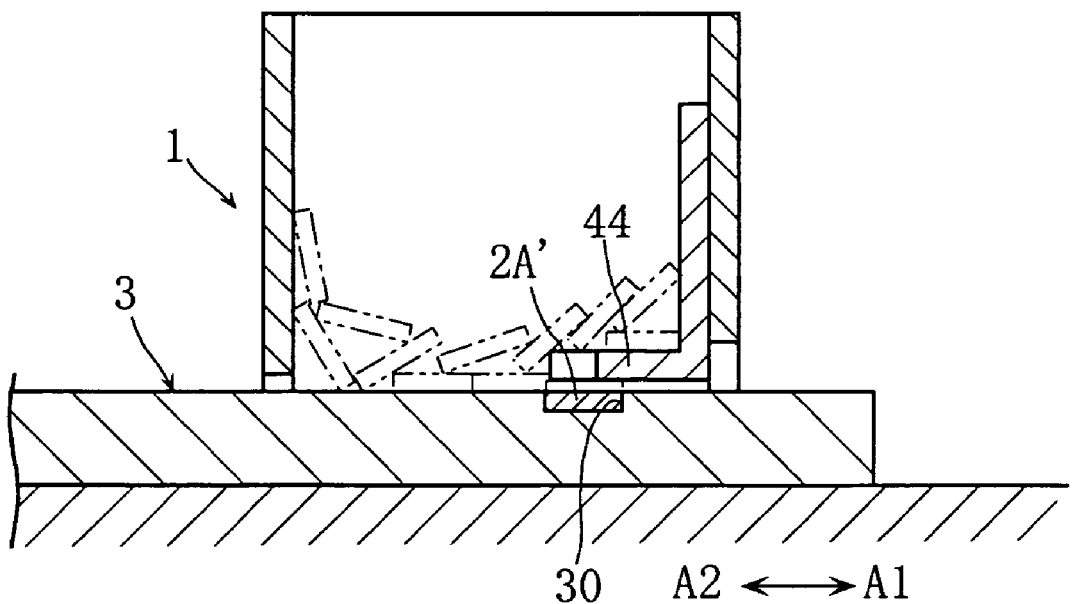

As described above, the test pieces 2A, 2B may be warped while stored in e.g. a bottle, and thus a warped test piece 2A' may be contained in the container 4. In this case, as shown in FIGS. 3A and 3B, the warped test piece 2A' may be caught in the recess 30. With the test piece supplying device 1, even such a warped test piece 2A', once caught in the recess 30, is taken out of the container 4 as the movable body 3 is moved in the direction A1, as shown in FIGS. 3-5, to be transferred to the optical checking position or any other destination.

More specifically, as shown in FIGS. 3A and 3B, when the test piece 2A' is accommodated in the recess 30, the test piece 2A' partly protrudes above the recess 30. In this state, when the movable body 3 is moved in the direction A1, the part of the test piece 2A' accommodated within the recess 30 is positioned below the sweep function portion 44, as shown in FIGS. 4A and 4B. When the movable body 3 is further moved in the direction A1, the sweep function portion 44 exerts a downward pressing force to the test piece 2A', and thus the part of the test piece 2A' protruding out of the recess 30 is flattened to be accommodated within the recess 30, whereby the test piece 2A' as a whole can pass below the sweep function portion 44. In this manner, in the test piece supplying device 1, even the warped test piece 2A' can be taken out of the container 4.

In the illustrated example, the warped test piece 2A' is partly accommodated in the recess 30 at one end at the side of the direction B1, while partly protruding above the recess 30 at the other end at the side of the direction B2. On the other hand, when the warped test piece 2A' is partly accommodated in the recess 30 at one end at the side of the direction B2, while partly protruding above the recess 30 at the other end at the side of the direction B1, the sweep function portion 44 scrapes the test piece 2A' out of the recess 30. However, after repeatedly moving the movable body, the test piece 2A' is finally reversed and the test piece 2A' is partly accommodated in the recess 30 at the end on the side of the direction B1. Thus, in the test piece supplying device 1, the test piece 2A' can be taken out of the container by repeatedly moving the movable body, regardless of how the test piece 2A' is warped or oriented in the recess 30. Further, the test piece 2A' can be reliably reversed with a high probability when the sweep function portion 44 strikes the test strip 2A' off the recess 30. Thus, in the test piece supplying device 1, the warped test piece 2A' can be taken out of the container by a smaller number of movements.

As described above, in the test piece supplying device 1, even the warped test piece 2A' is reliably taken out of the container 4. Thus, even if some warped test pieces 2A' are contained in the container 4, the test pieces 2A, 2A', 2B can still be taken out properly, thereby improving the efficiency in taking out the test pieces 2A, 2A', 2B from the container 4.

In the above-described test piece supplying device 1, the interference surface or edge 44a of the sweeping means 41 is inclined, though this may be variously modified. For example, the sweeping means can be formed as illustrated in FIGS. 6-13.

Figure 6:
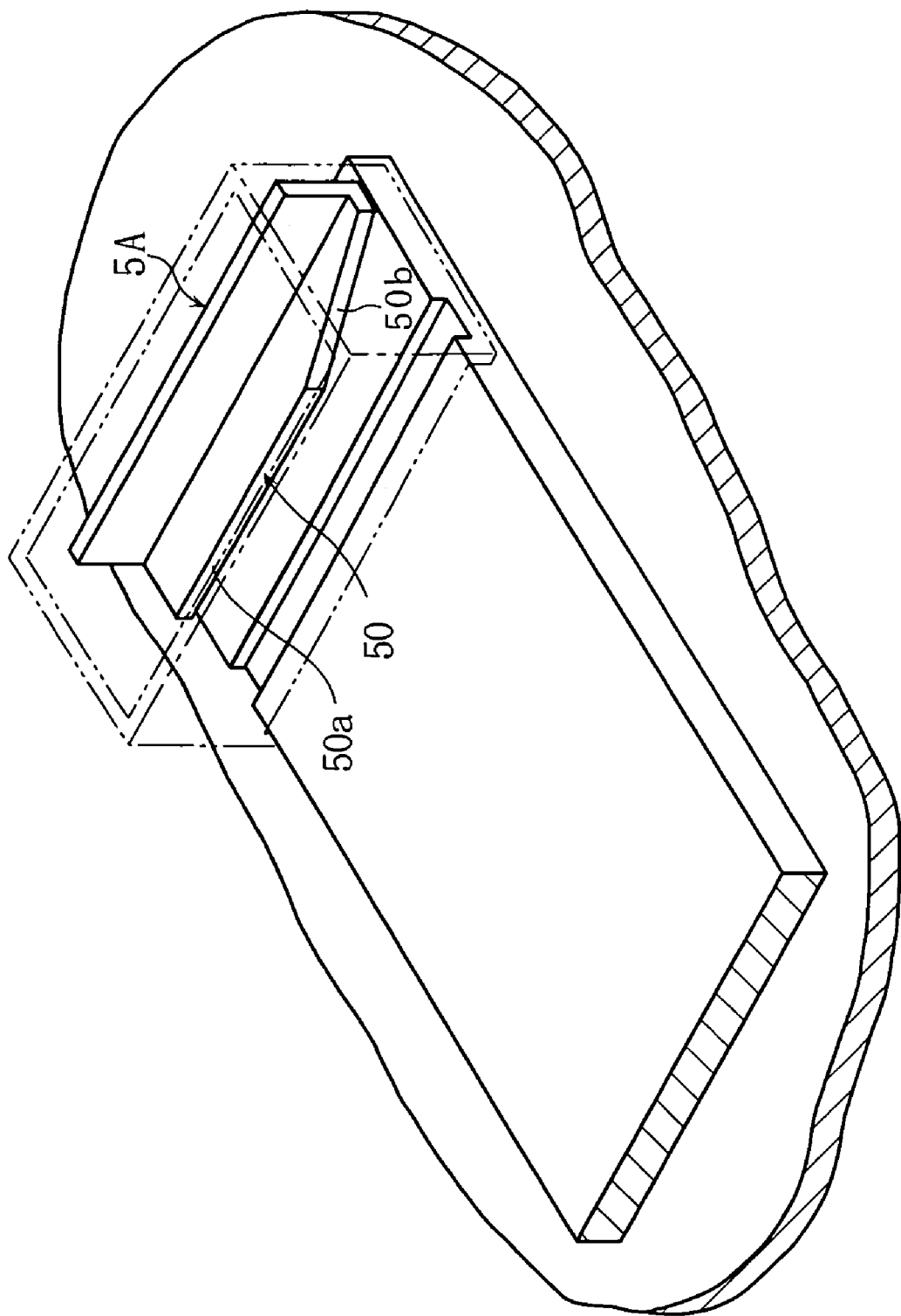
FIG. 6 is a perspective view illustrating another example of sweeping means.
Figure 7:
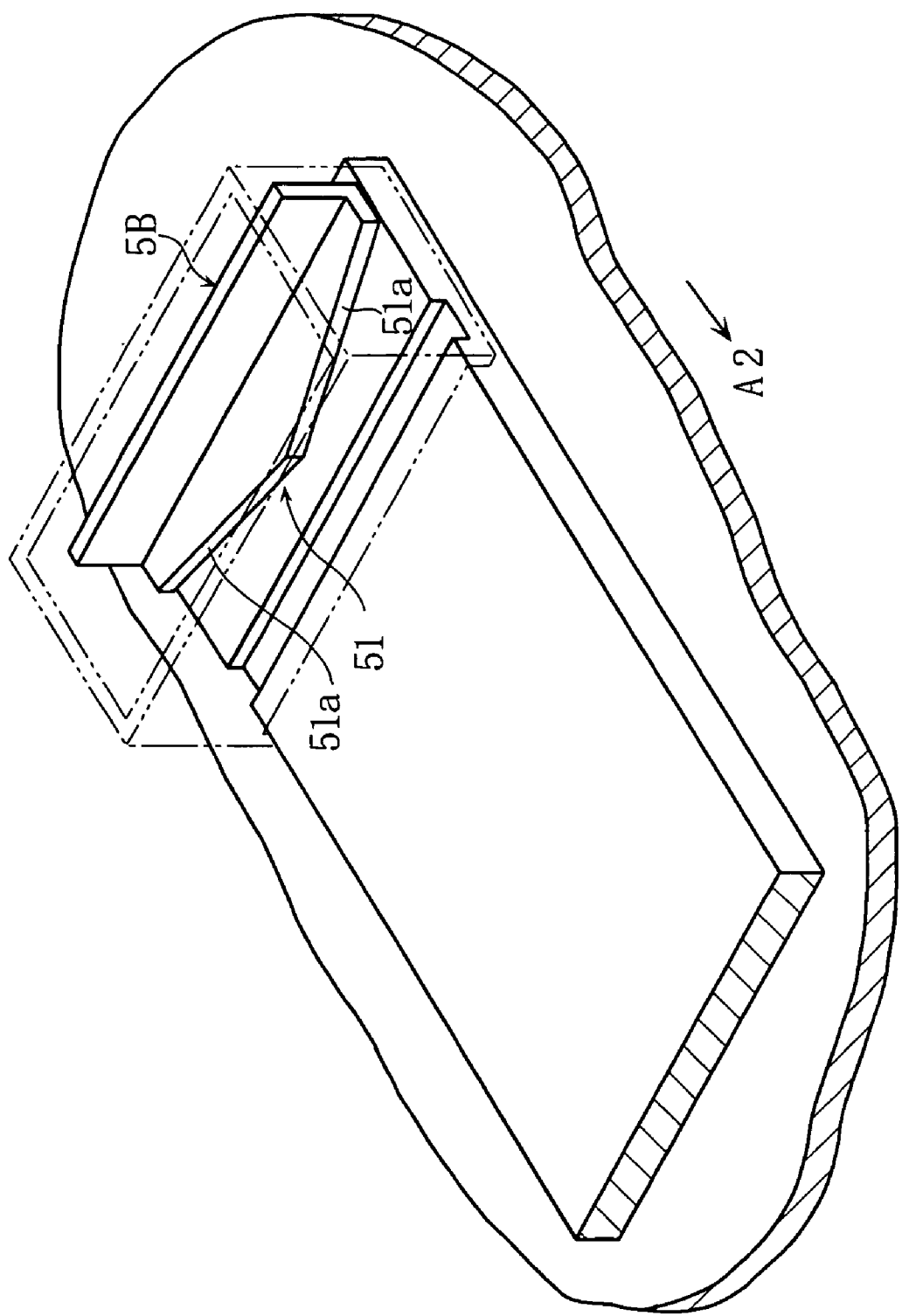
FIG. 7 is a perspective view illustrating another example of the sweeping means.
Figure 8:
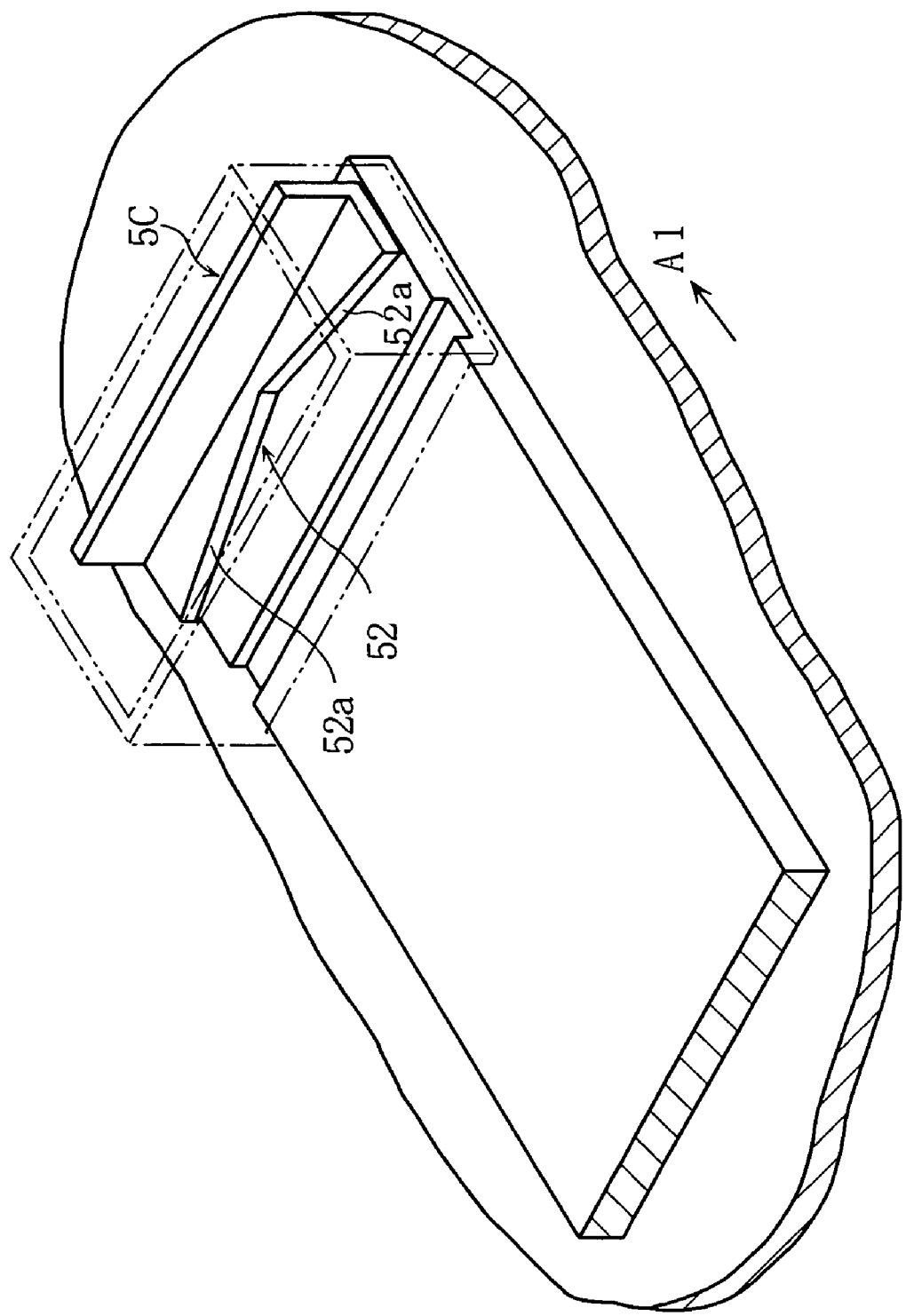
FIG. 8 is a perspective view illustrating another example of the sweeping means.
Figure 9:
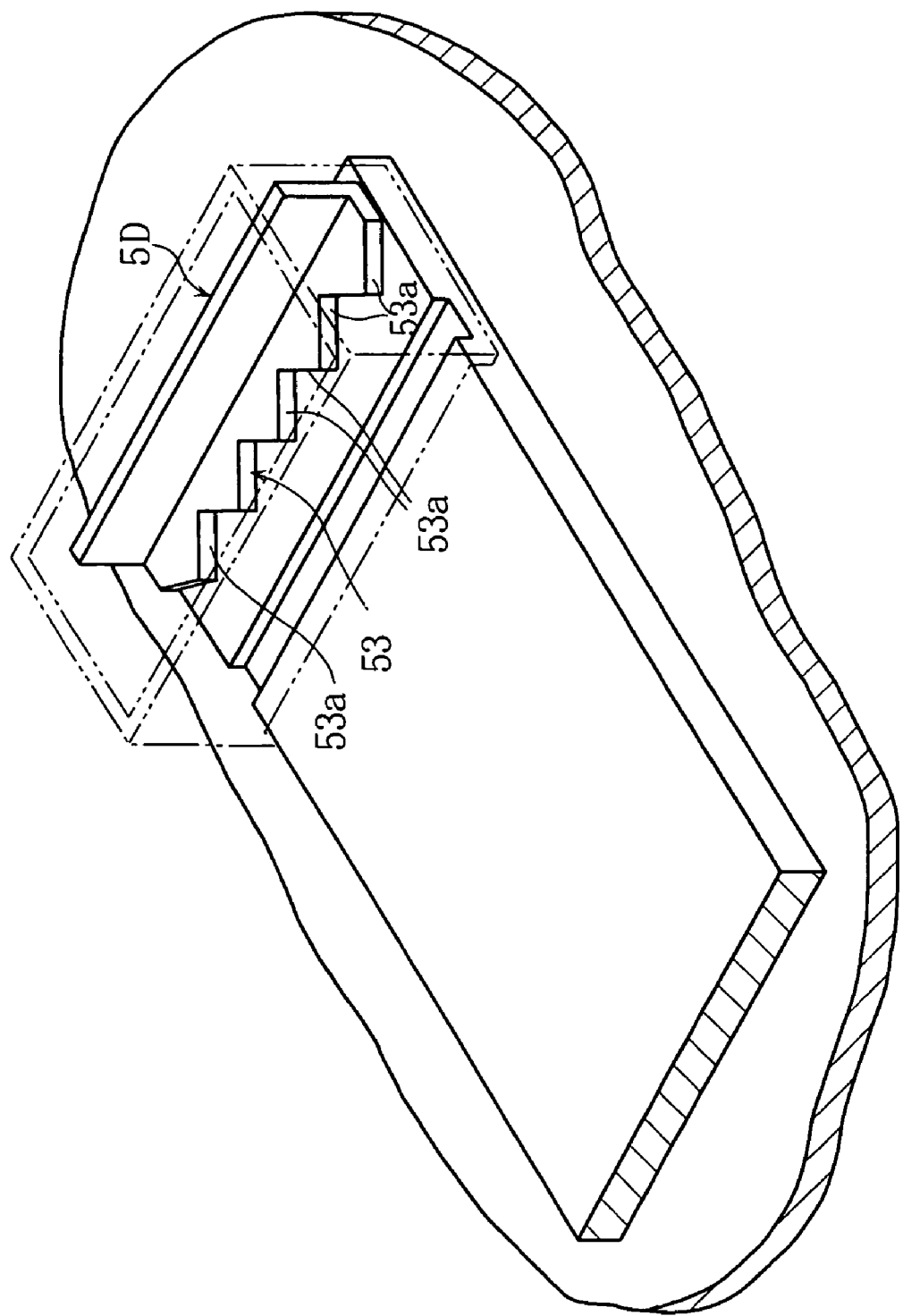
FIG. 9 is a perspective view illustrating another example of the sweeping means.
Figure 10:
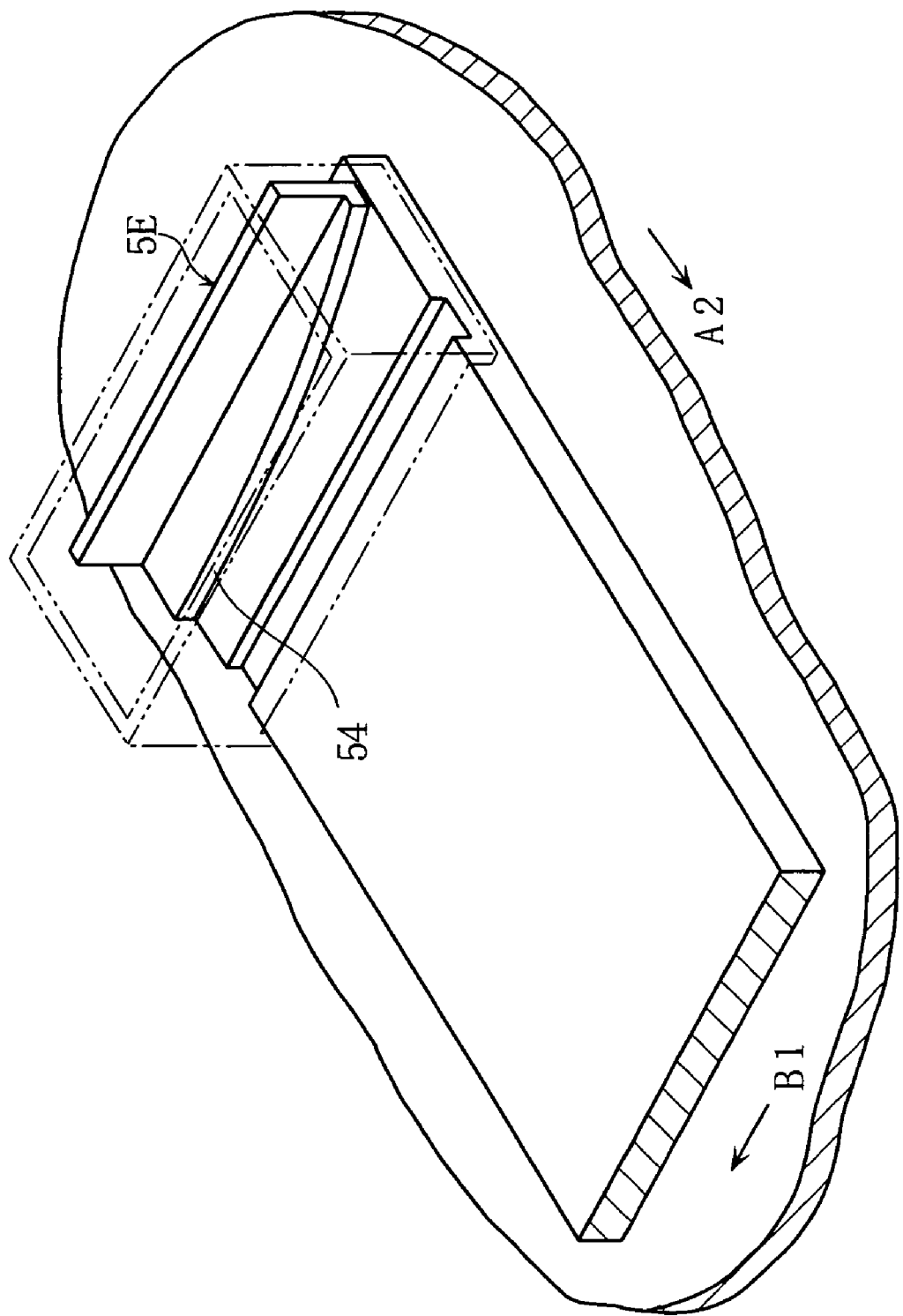
FIG. 10 is a perspective view illustrating another example of the sweeping means.
Figure 11:
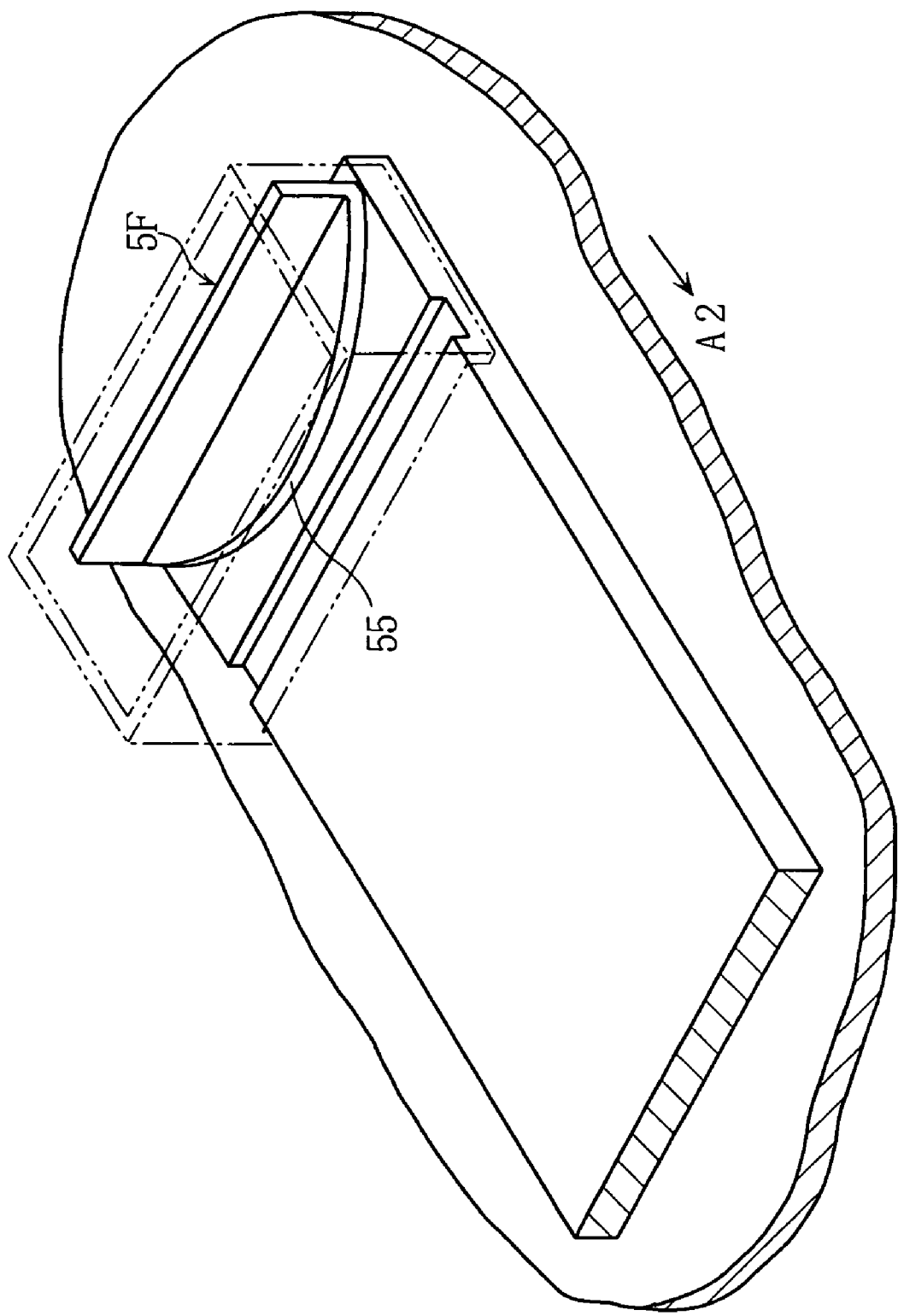
FIG. 11 is a perspective view illustrating another example of the sweeping means.
Figure 12:
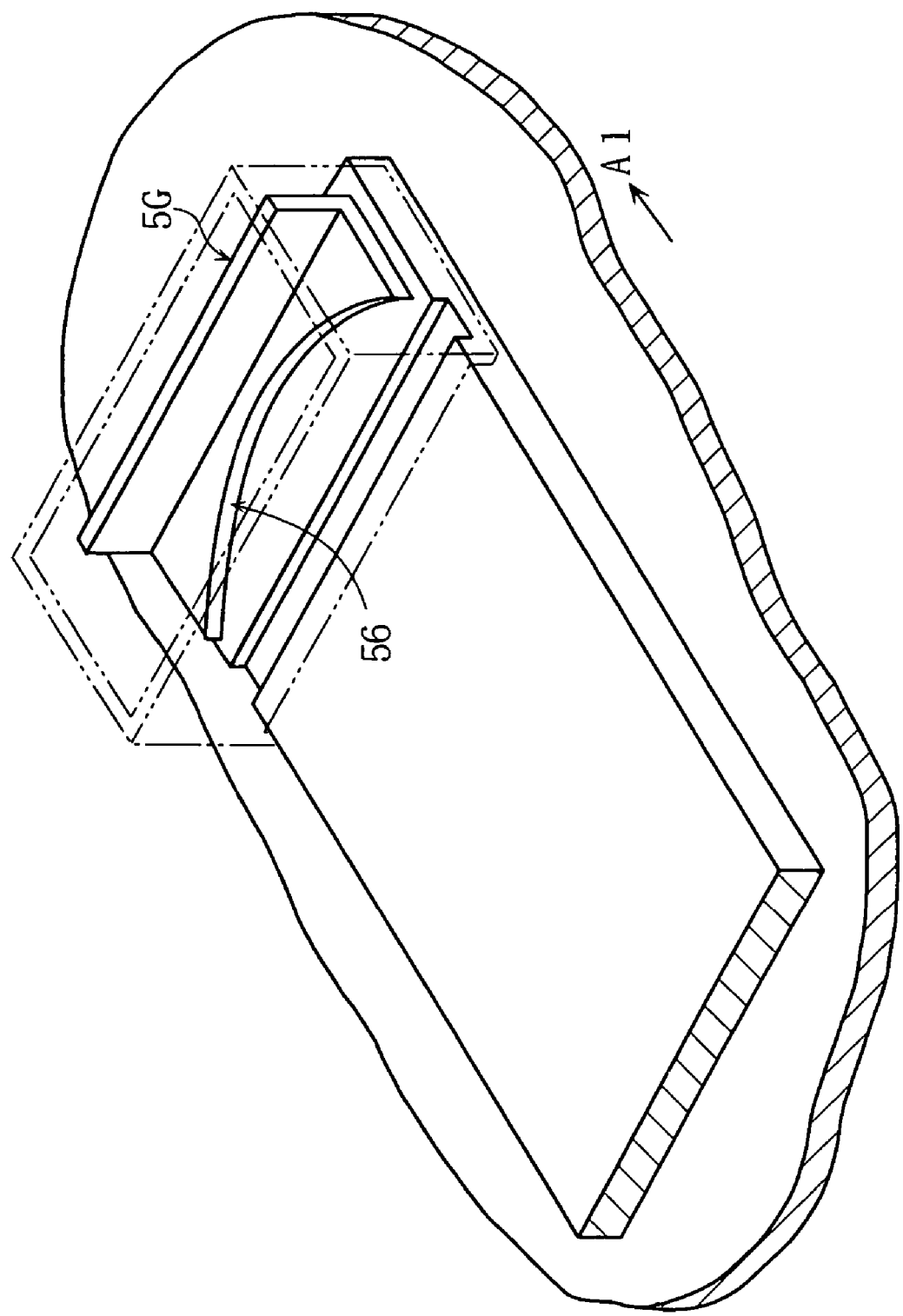
FIG. 12 is a perspective view illustrating another example of the sweeping means.
Figure 13:
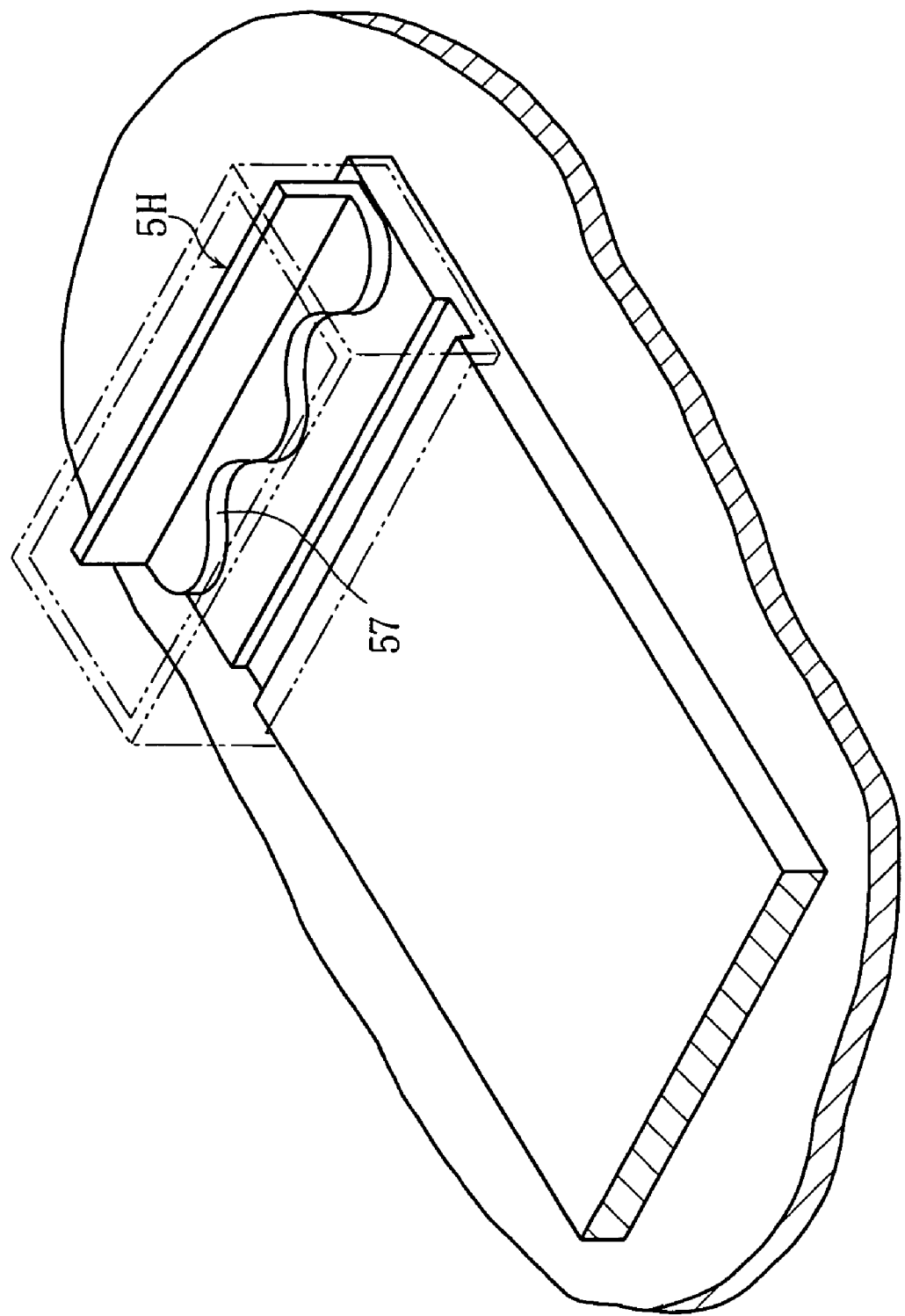
FIG. 13 is a perspective view illustrating another example of the sweeping means.
Figure 14A:
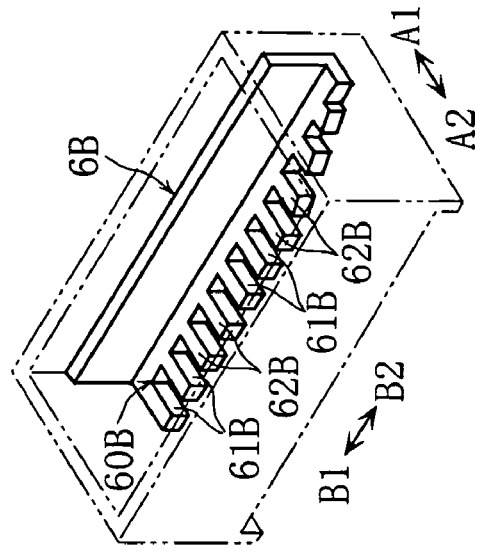
FIG. 14A-E is a perspective view illustrating another example of the sweeping means.
Figure 14B:
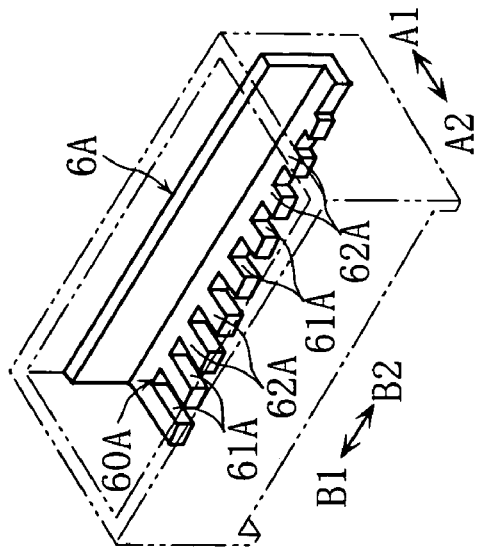
Figure 14E:
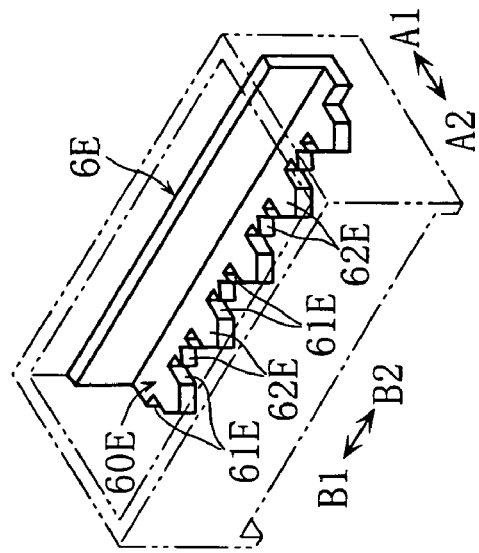
Figure 14D:
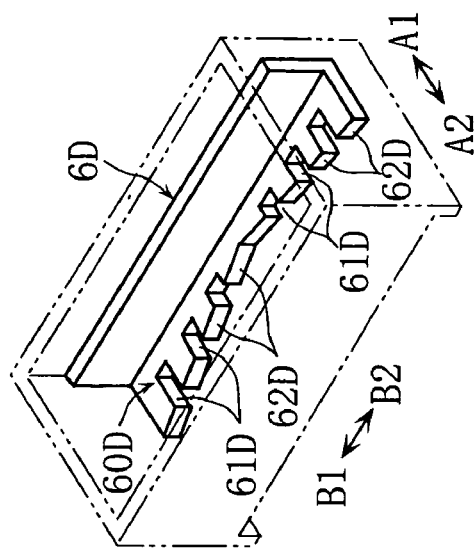
Figure 14C:
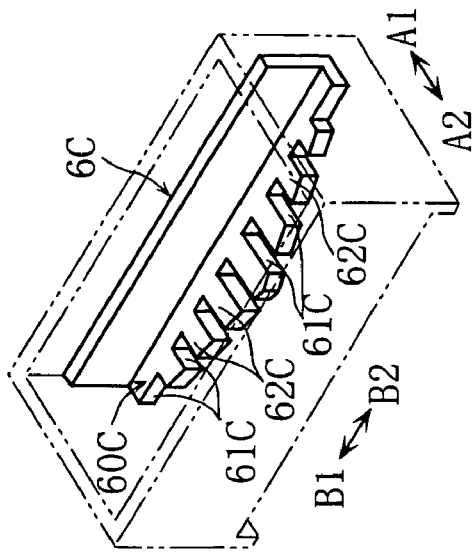
Figure 15A:
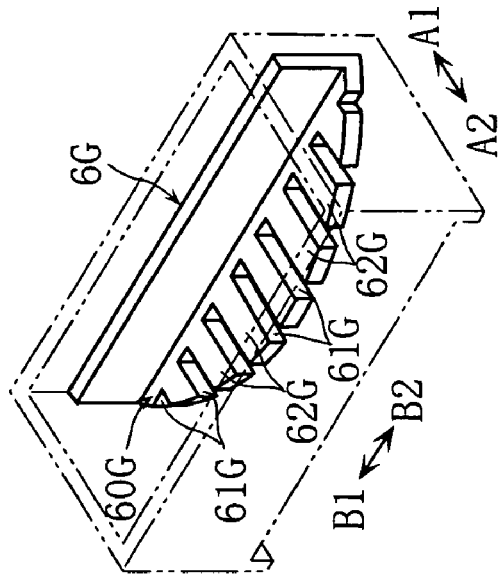
FIG. 15A-D is a perspective view illustrating another example of the sweeping means.
Figure 15B:
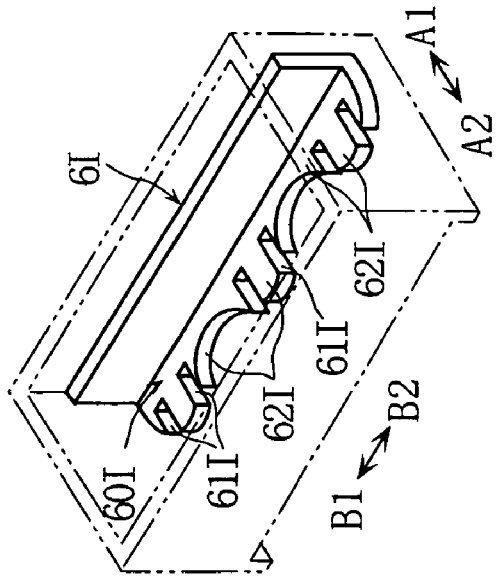
Figure 15C:
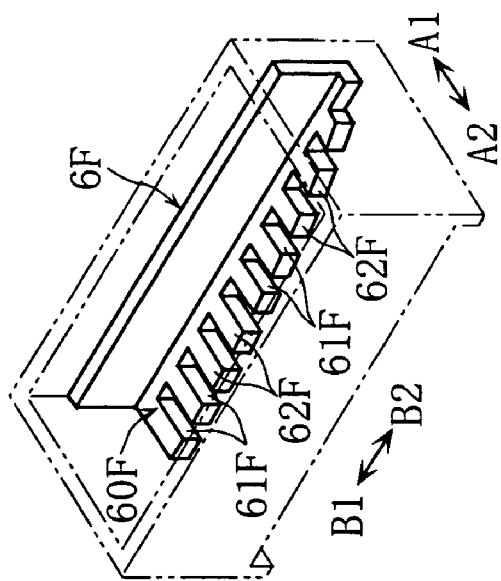
Figure 15D:
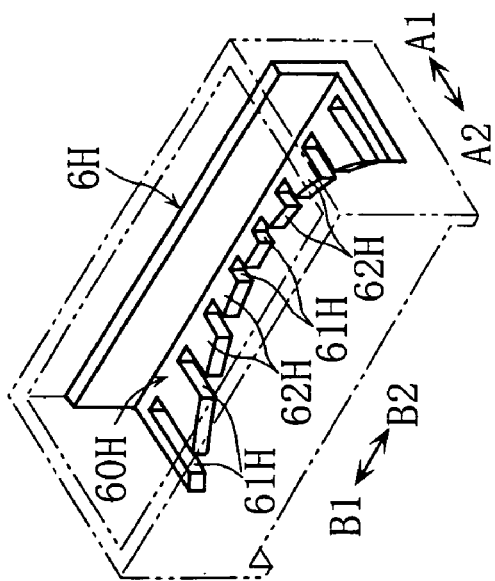

The sweeping means 5A shown in FIG. 6 includes an interference surface 50 that is a combination of a flat surface 50a and an inclined surface 50b. The sweeping means 5B shown in FIG. 7 includes an interference surface 51 that is a combination of two inclined surfaces 51a forming a bending surface having an intermediate convex portion protruding in the direction A2. The sweeping means 5C shown in FIG. 8 includes an interference surface 52 that is a combination of two inclined surfaces 52a forming a bending surface having an intermediate concave portion retracting in the direction A1. The sweeping means 5D shown in FIG. 9 includes an interference surface 53 that is a combination of a plurality of inclined surfaces 53a forming corrugations each pointing sharply. The sweeping means 5E shown in FIG. 10 includes an interference surface 54 that is a smoothly curved surface bulging in the direction A2 at an end on the side of the direction B1. The sweeping means SF shown in FIG. 11 includes an interference surface 55 that is a convex surface protruding in the direction A2 and having an intermediate vertex. The sweeping means 5G shown in FIG. 12 includes an interference surface 56 that is a concave surface having an intermediate bottom retracting in the direction A1. The sweeping means 5H shown in FIG. 13 includes an interference surface 57 that is rippled.

Further, the sweeping means of the container may be formed as shown in FIGS. 14A-14E, 15A-15D, 16A-16E, and 17-19.

Each of sweeping means 6A-6I shown in FIGS. 14A-14E, 15A-15D includes a respective one of the sweep function portions 60A-60I, respectively formed with a plurality of cutouts 61A-61I each elongated in the directions A1, A2 and arranged at intervals in the directions B1, B2. In other words, the sweeping means 6A-6I are respectively formed with a plurality of interference portions 62A-62I each projecting in the direction A2.

The sweeping means 6A-6E shown in FIGS. 14A-14E are made of the sweep function portions shown in FIG. 6-9, by forming the plurality of cutouts 61A-61E respectively. The sweeping means 6F-6I shown in FIGS. 15A-15D are made of the sweep function portions shown in FIG. 10-13, by forming the plurality of cutouts 61F-61I respectively.

Of course, the position, the number, and the dimension of the cutouts, and also the original form of the sweep function portions to be formed with the cutouts are not limited to the above-described examples, and these may be variously modified as long as the object of the present invention is attained.

Each of sweeping means 7A-7E shown in FIGS. 16A-16E includes a plurality of pins 70A-70E attached to a respective one of attaching portions 71A-71E in a manner such that the pins project in the direction A2 and are aligned in the directions B1, B2. Each of the pins 70A-70E includes a hemispheric tip end.

In the illustrated sweeping means 7A-7E, at least a part of the pins 70A-70E have tip ends differently positioned in the directions A1, A2. The positions of the pins 70A-70E generally correspond to the positions of the interference portions 62A-62E shown in FIGS. 14A-14E.

Of course, the pins may be positioned the same as or similarly to the positions of the interference portions 62F-62I shown in FIGS. 15A-15D, or may be positioned otherwise as long as the object of the present invention is attained.

Figure 17:
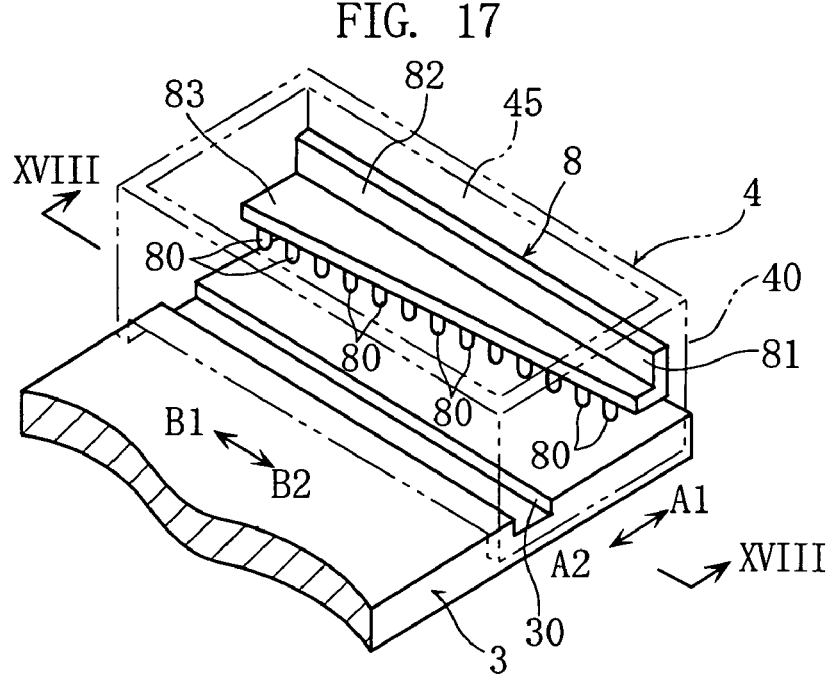
FIG. 17 is a perspective view illustrating another example of the sweeping means.
Figure 18:
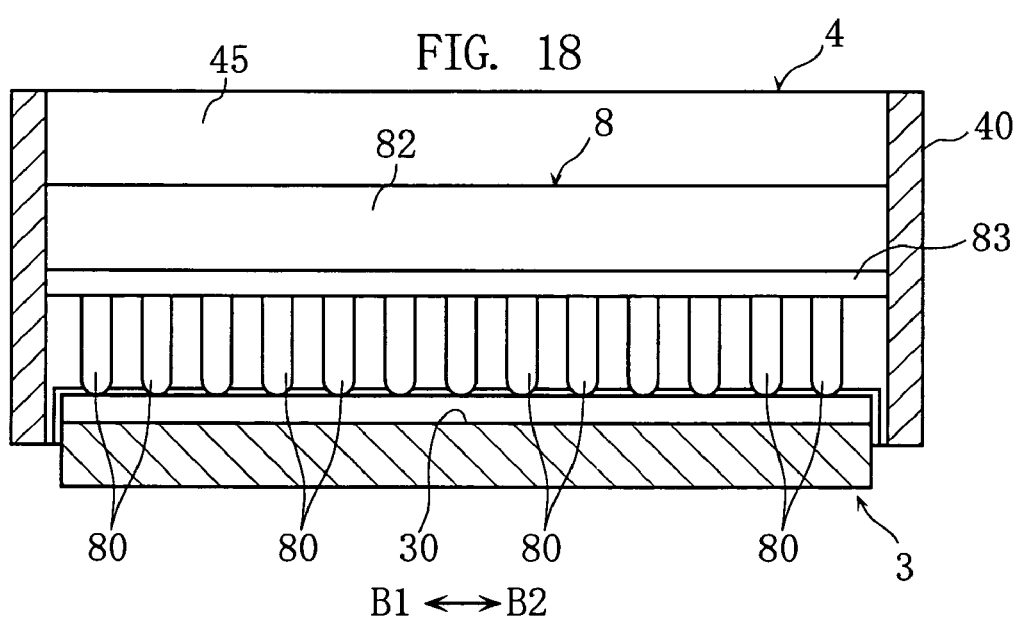
FIG. 18 is a sectional view taken along lines XVIII-XVIII in FIG. 17.
Figure 19:
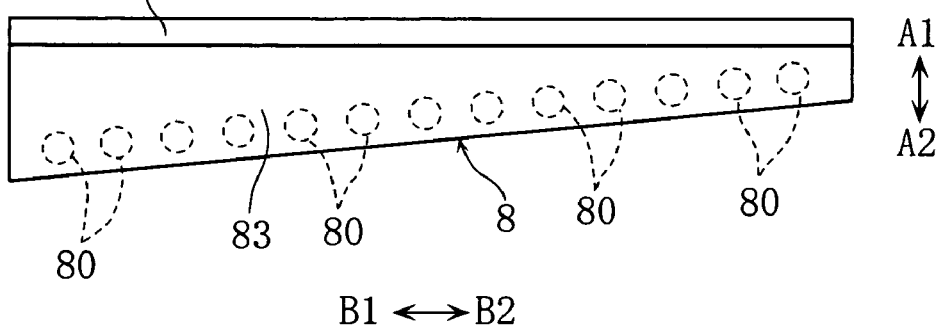
FIG. 19 is a plan view illustrating the sweeping means of FIGS. 17 and 18.

The sweeping means 8 shown in FIGS. 17-19 includes an attaching portion 81 provided with a plurality of pins 80 projecting downward therefrom.

The pins 80 interferes with and removes the test piece brought right above the test piece accommodated in the recess 30 of the movable body 3. The attaching portion 81 fixes the pins 80 to the body 40 of the container 4, and includes a vertical portion 82 fixed to a wall 45 of the body 4 of the container 4, and also includes a horizontal portion 83 to which the pins 80 are fixed.

The horizontal portion 83 is a plate whose dimension in the directions A1, A2 is reduced as proceeding in the direction B2, similarly to the sweep function portion 44 of the sweeping means 41 shown in FIG. 1. The pins 80 are fixed to the horizontal portion 83 along the end at the side of the direction A2. In other words, as well shown in FIG. 19, the pins 80 are positioned on a line inclined relative to the directions B1, B2.

Of course, the pins may be fixed to the sweeping means 5A-5H shown in FIGS. 6-13 along the ends at the side of the direction A2, or may be positioned otherwise as long as the object of the present invention is attained.

Figure 20:
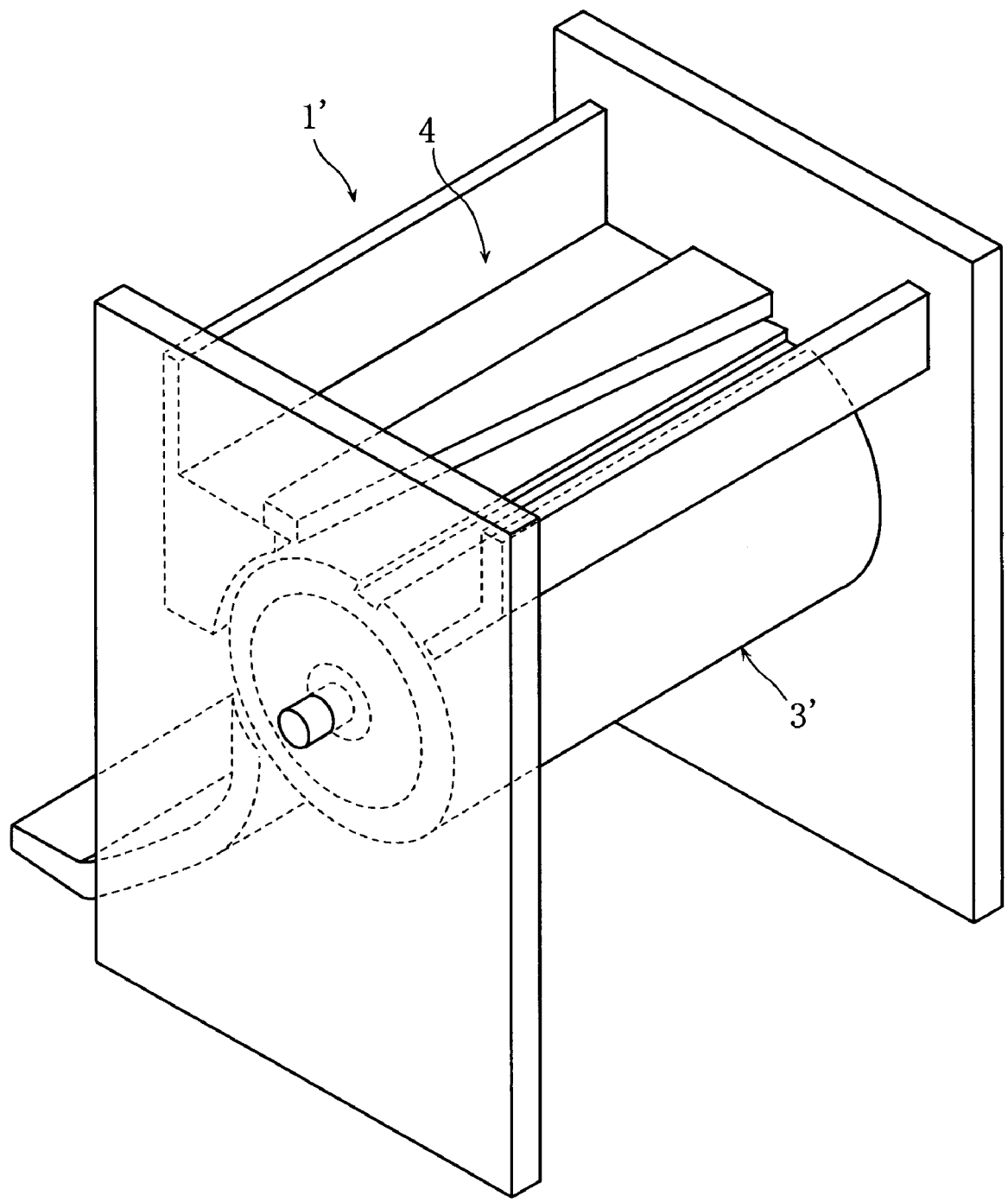
FIG. 20 is a perspective view illustrating another example of the test piece supplying device.
Figure 21:
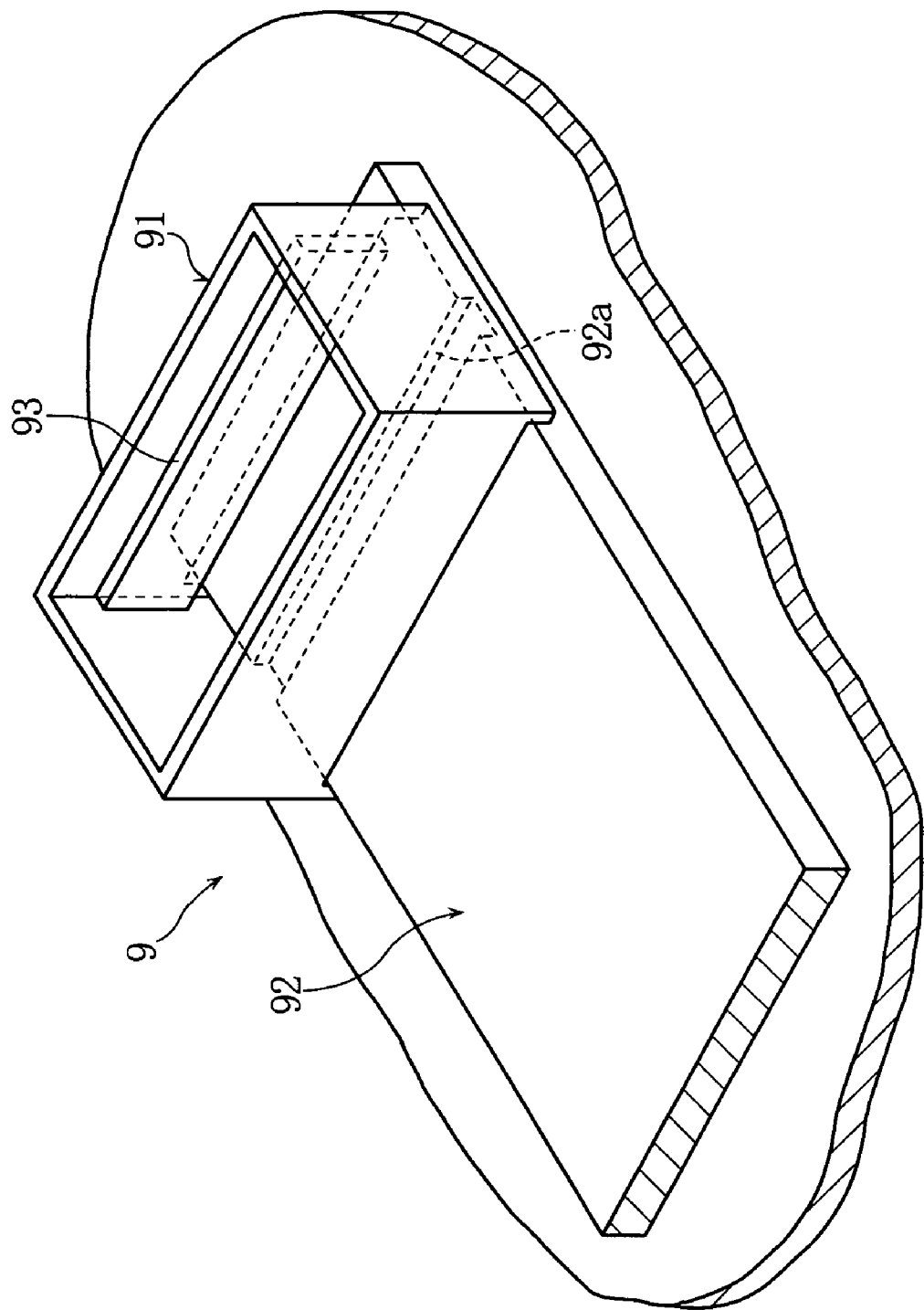
FIG. 21 is a perspective view illustrating an example of a conventional test piece supplying device.
Figure 22A:
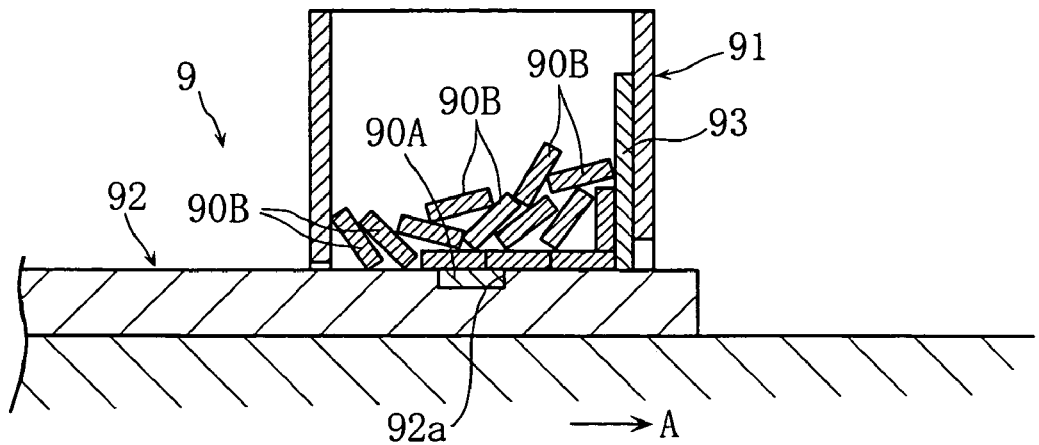
FIG. 22A-C is a sectional view illustrating the function of the test piece supplying device shown in FIG. 21.
Figure 22B:
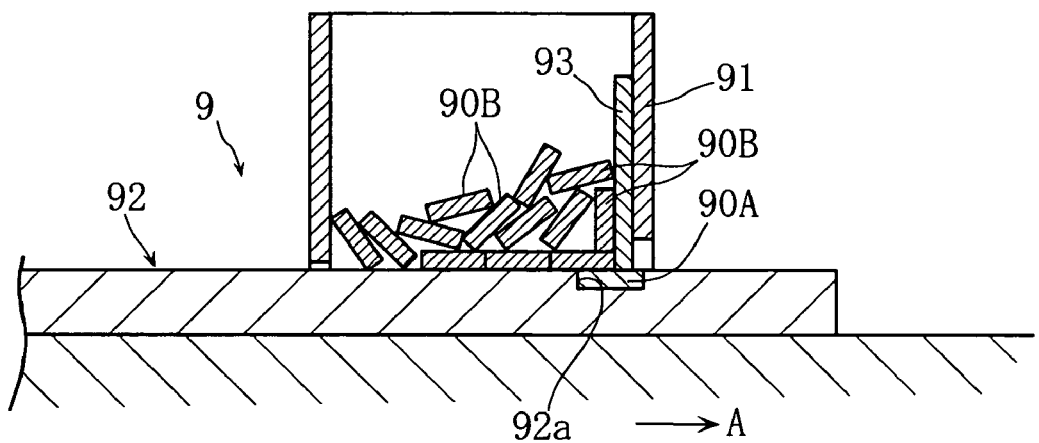
Figure 22C:
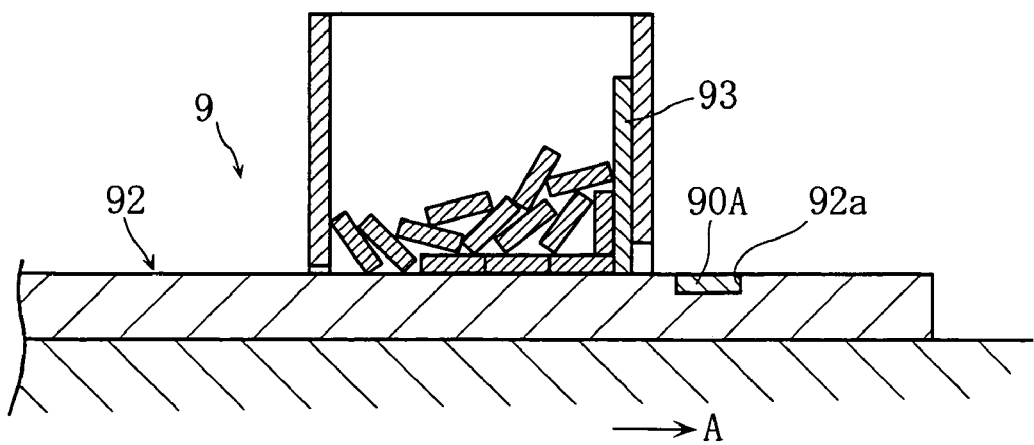
Figure 23:
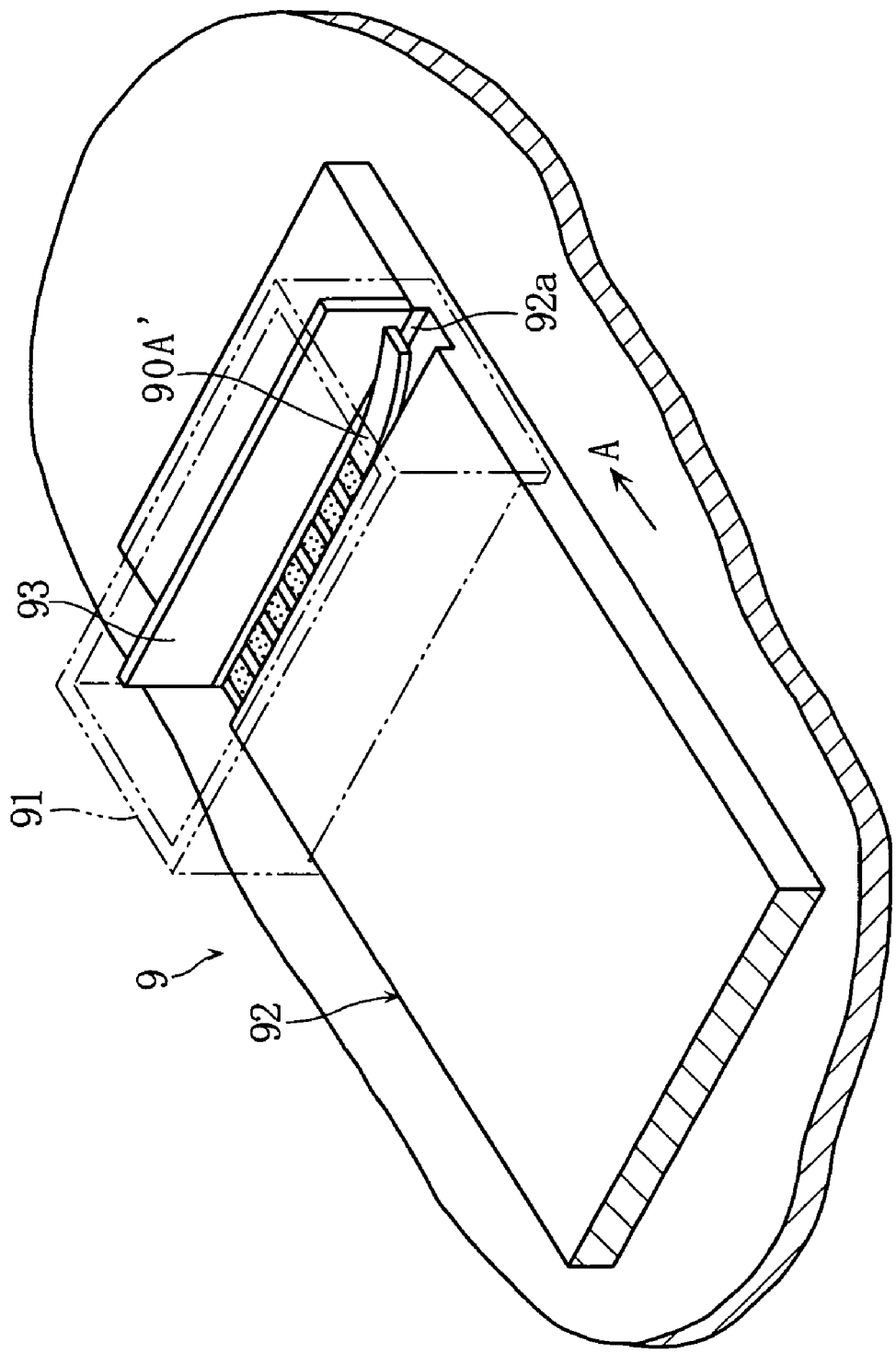
FIG. 23 is a perspective view illustrating the problem of the test piece supplying device shown in FIG. 21.

As shown in FIG. 20, the present invention may also be applied to a test piece supplying device 1' including a rotating body 3' rotating for taking a test piece out of the container 4. In the test piece supplying device 1' shown FIG. 20, the interference surface of the sweeping means is formed as an inclined surface, though may be formed as the sweeping means described above with reference to FIGS. 6-13. Further, the sweeping means of the test piece supplying device 1' may be formed as the sweeping means described above with reference to FIGS. 14-19, or may be formed otherwise as long as the object of the present invention is attained.

The invention claimed is:

1. An analytical testing element supplying device comprising:
   a container for containing a plurality of analytical testing elements; and
   a movable body formed with an elongated recess for accommodating one of the analytical testing elements contained in the container; the movable body being moved relative to the container with one analytical testing element accommodated in the recess, so that the analytical testing elements, one at a time, are taken out of the container,
   wherein the container is provided with a horizontally extending plate that interferes with loose analytical testing elements above a secured testing element accommodated in the recess when the movable body moves relative to the container,
   wherein the horizontally extending plate includes an interference surface for interfering with the loose testing elements, the interference surface having a portion non-parallel to a longitudinal direction of the recess,
   wherein when the secured testing element is warped and partly protrudes from the recess, a portion of the horizontally extending plate that is adjacent to the interference surface comes into contact with the secured testing element for flattening the secured testing element into the recess when the movable body moves relative to the container.

2. The analytical testing element supplying device according to claim 1, wherein the recess is elongated in a direction perpendicular to a transfer direction of the analytical testing elements.

3. The analytical testing element supplying device according to claim 2, wherein the interference surface includes a linear portion inclined to the elongated recess or a curved portion.

4. An analytical testing element supplying device comprising:
   a container for containing a plurality of analytical testing elements; and
   a movable body formed with a recess for accommodating one of the testing elements contained in the container; the movable body being moved relative to the container with one testing element accommodated in the recess, so that the testing elements, one at a time, are taken out of the container;
   wherein the container is provided with a plurality of interference portions that interfere with loose testing elements above a secured testing element accommodated in the recess when the movable body moves relative to the container, the interference portions projecting in a direction intersecting a vertical direction
   wherein when the secured testing element is warped and partly protrudes from the recess, the interference portions conic into contact with the secured testing element for flattening the secured testing element into the recess when the movable body moves relative to the container.

5. The analytical testing element supplying device according to claim 4, wherein at least a part of the plurality of interference portions project by different distances.

6. The analytical testing element supplying device according to claim 4, wherein the recess is elongated in a direction perpendicular to the transfer direction of the analytical testing elements,
   wherein at least a part of the plurality of interference portions are arranged so that the shortest distances between tip ends of the interference portions and the recess are different from each other.

7. The analytical testing element supplying device according to claim 6, wherein the part of the plurality of interference portions are arranged in a straight line or a substantially straight line inclined relative to the elongated recess, or in a curve or a substantially curved line.

8. The analytical testing element supplying device according to claim 4, wherein the plurality of interference portions are provided by forming a plurality of cutouts in a horizontally extending plate.

9. The analytical testing element supplying device according to claim 4, wherein the plurality of interference portions are provided by a plurality of fixed pins.

10. An analytical testing element supplying comprising:
    a container for containing a plurality of analytical testing elements and a movable body formed with a recess for accommodating one of the testing elements contained in the container; the movable body being moved relative to the container with one testing element accommodated in the recess, so that the testing elements, one at a time, are taken out of the container;
    wherein the container is provided with interfering means that interfere with loose testing elements above a secured testing element in the recess when the movable body moves relative to the container,
    wherein when the secured testing element is warped and partly protrudes from the recess, the interfering means come into contact with the secured testing element for flattening the secured testing element into the recess when the movable body moves relative to the container,
    wherein the recess is elongated in a direction perpendicular to a transfer direction of the analytical testing elements,
    wherein the interfering means are provided with a plurality of pins projecting downward,
    wherein at least a part of the plurality of pins are arranged so the shortest distance between tip ends of the pins and the recess are different from each other.

11. The analytical testing element supplying device according to claim 10, wherein the part of the plurality of pins are arranged in a straight or substantially straight line inclined relative to the elongated recess, or in a curve or substantially curved line.

12. The analytical testing element supplying device according to claim 1, wherein the movable body moves horizontally to take the secured analytical testing element out of the container.

13. The analytical testing element supplying device according to claim 1, wherein the movable body rotates to take the secured analytical testing element out of the container.

14. The analytical testing element supplying device according to claim 4, wherein the movable body moves horizontally to take the secured testing element out of the container.

15. The analytical testing element supplying device according to claim 4, wherein the movable body rotates to take the secured testing element out of the container.

16. The analytical testing element supplying device according to claim 10, wherein the movable body moves horizontally to take the secured testing element out of the container.

17. The analytical testing element supplying device according to claim 10, wherein the movable body rotates to take the secured testing element out of the container.

* * * * *